United States Patent
Kido et al.

(10) Patent No.: US 10,357,630 B2
(45) Date of Patent: Jul. 23, 2019

(54) LIGHTING APPARATUS, LUMINAIRE, AND ELECTRONIC APPARATUS

(71) Applicants: Panasonic Corporation, Osaka (JP); Nintendo Co., Ltd., Kyoto (JP)

(72) Inventors: Hiroshi Kido, Osaka (JP); Shigeru Ido, Osaka (JP); Hisao Kataoka, Osaka (JP); Sadayoshi Hattori, Kyoto (JP)

(73) Assignees: PANASONIC CORPORATION, Osaka (JP); NINTENDO CO., LTD., Kyoto (JP)

( * ) Notice: Subject to any disclaimer, the term of this patent is extended or adjusted under 35 U.S.C. 154(b) by 0 days.

(21) Appl. No.: 15/904,321

(22) Filed: Feb. 24, 2018

(65) Prior Publication Data
US 2018/0250493 A1    Sep. 6, 2018

(30) Foreign Application Priority Data
Mar. 1, 2017    (JP) .................................. 2017-038828

(51) Int. Cl.
H05B 37/02    (2006.01)
H05B 33/08    (2006.01)
(Continued)

(52) U.S. Cl.
CPC .............. *A61M 21/02* (2013.01); *G08B 5/36* (2013.01); *H05B 33/086* (2013.01);
(Continued)

(58) Field of Classification Search
None
See application file for complete search history.

(56) References Cited

U.S. PATENT DOCUMENTS

| | | | |
|---|---|---|---|
| 2004/0052076 A1* | 3/2004 | Mueller | F21V 23/0442 362/293 |
| 2009/0278476 A1* | 11/2009 | Baaijens | H05B 33/0863 315/297 |

(Continued)

FOREIGN PATENT DOCUMENTS

| | | |
|---|---|---|
| DE | 102014216491 A1 | 2/2015 |
| EP | 2934071 A1 | 10/2015 |

(Continued)

OTHER PUBLICATIONS

Extended European search report dated Jul. 18, 2018 issued for the corresponding European patent application No. 18158818.7.

*Primary Examiner* — Crystal L Hammond
(74) *Attorney, Agent, or Firm* — Renner, Otto, Boisselle & Sklar, LLP

(57) ABSTRACT

A lighting apparatus includes: an illuminator including a light source which emits illumination light; a lighting controller which controls the illuminator; and a receiver which receives, from a control apparatus, a control command signal generated based on at least one of user information and environmental information in order to control the illumination light of the illuminator, wherein the control command signal received by the receiver includes one or more parameters including, as an element, at least one of a brightness of the illumination light of the illuminator, a color temperature of the illumination light of the illuminator, and control time for controlling the illumination light of the illuminator.

26 Claims, 18 Drawing Sheets

(51) Int. Cl.
*G08B 5/36* (2006.01)
*A61M 21/02* (2006.01)
*A61M 21/00* (2006.01)
*A61N 5/06* (2006.01)

(52) U.S. Cl.
CPC ..... *H05B 33/0872* (2013.01); *H05B 37/0218* (2013.01); *H05B 37/0272* (2013.01); *H05B 37/0281* (2013.01); *A61M 2021/0044* (2013.01); *A61M 2021/0083* (2013.01); *A61N 2005/0663* (2013.01); *Y02B 20/42* (2013.01)

(56) References Cited

U.S. PATENT DOCUMENTS

| | | | | |
|---|---|---|---|---|
| 2012/0235579 | A1* | 9/2012 | Chemel | F21S 2/005 |
| | | | | 315/152 |
| 2015/0054965 | A1* | 2/2015 | Sudo | H04N 5/23219 |
| | | | | 348/169 |
| 2015/0296596 | A1* | 10/2015 | Lee | H05B 37/0227 |
| | | | | 315/297 |
| 2016/0366746 | A1* | 12/2016 | van de Ven | F21V 29/74 |
| 2018/0027637 | A1* | 1/2018 | Kurt | H05B 33/0857 |
| | | | | 315/159 |

FOREIGN PATENT DOCUMENTS

| | | |
|---|---|---|
| JP | 2003-275315 A | 9/2003 |
| WO | 2008/001289 A2 | 1/2008 |
| WO | 2016/131714 A1 | 8/2016 |

\* cited by examiner

FIG. 3

| CONTROL COMMAND SIGNAL | FIRST PARAMETER | | SECOND PARAMETER | | THIRD PARAMETER | |
|---|---|---|---|---|---|---|
| | TYPE | RANGE | TYPE | RANGE | TYPE | RANGE |
| TURN-ON SIGNAL (A1) | BRIGHTNESS | 5 - 100 [%] | COLOR TEMPERATURE | 2000 - 6500 [K] | CONTROL TIME | 0 - 200 [× 0.1 s] |
| UP/DOWN SIGNAL (A2) | BRIGHTNESS | 5 - 100 [%] | COLOR TEMPERATURE | 2000 - 6500 [K] | CONTROL TIME | 0 - 120 [× 0.5 s] |
| TURN-OFF SIGNAL (A3) | CONTROL TIME | 0 - 200 [× 0.1 s] | — | — | — | — |
| LIGHT ALARM SIGNAL (B1) | CONTROL TIME | 10 - 30 [× 1 min] | BRIGHTNESS | 5 - 100 [%] | — | — |
| LIGHT ALERT SIGNAL (C1) | INTERVAL | 10 - 30 [× 1 min] | THE NUMBER OF TIMES | 1 - 5 [TIME(S)] | — | — |
| FLUCTUATION SIGNAL (D1) | CONTROL TIME | 1 - 10 [× 1 min] | BRIGHTNESS | 0 - 50 [%] | COLOR TEMPERATURE | 2000 - 6500 [K] |

LIGHTING APPARATUS, LUMINAIRE, AND ELECTRONIC APPARATUS

CROSS REFERENCE TO RELATED APPLICATION

This application claims the benefit of priority of Japanese Patent Application Number 2017-038828 filed on Mar. 1, 2017, the entire content of which is hereby incorporated by reference.

BACKGROUND

1. Technical Field

The present disclosure relates to a lighting apparatus, a luminaire including the lighting apparatus, and an electronic apparatus including the lighting apparatus.

2. Description of the Related Art

In recent years, products or systems for improving quality of life (QOL) desired by users in daily life have been studied.

For example, a luminaire capable of improving QOL by irradiating a user with illumination light according to a vital rhythm such as a circadian rhythm having approximately one day as a cycle has been proposed (Japanese Unexamined Patent Application Publication No. 2003-275315).

SUMMARY

However, a conventional luminaire cannot change illumination light unless a user operates the luminaire. In addition, the user does not know illumination light suitable for the user himself/herself and an environment, and thus the user cannot easily change to such illumination light suitable for the user himself/herself and the environment.

The present disclosure was made to solve the problem, and has an object to provide a lighting apparatus etc. capable of irradiating a user with illumination light suitable for the user and an environment without requiring any user operation.

In order to achieve the above object, a lighting apparatus according to an aspect of the present disclosure includes: an illuminator including a light source which emits illumination light; a lighting controller which controls the illuminator; and a receiver which receives, from another apparatus, a control command signal generated based on at least one of user information and environmental information in order to control the illumination light, wherein the control command signal includes one or more parameters including, as an element, at least one of a brightness of the illumination light, a color temperature of the illumination light, and control time for controlling the illumination light.

In addition, a luminaire according to an aspect of the present disclosure includes the lighting apparatus.

In addition, an electronic apparatus according to an aspect of the present disclosure includes the lighting apparatus.

According to the present disclosure, it is possible to irradiate a user with illumination light suitable for the user and the environment without requiring the user to operate the lighting apparatus.

BRIEF DESCRIPTION OF DRAWINGS

The figures depict one or more implementations in accordance with the present teaching, by way of examples only, not by way of limitations. In the figures, like reference numerals refer to the same or similar elements.

FIG. 3 is a diagram illustrating examples of control command signals for use by the lighting system according to Embodiment 1;

DETAILED DESCRIPTION OF THE EMBODIMENTS

Figure 1:
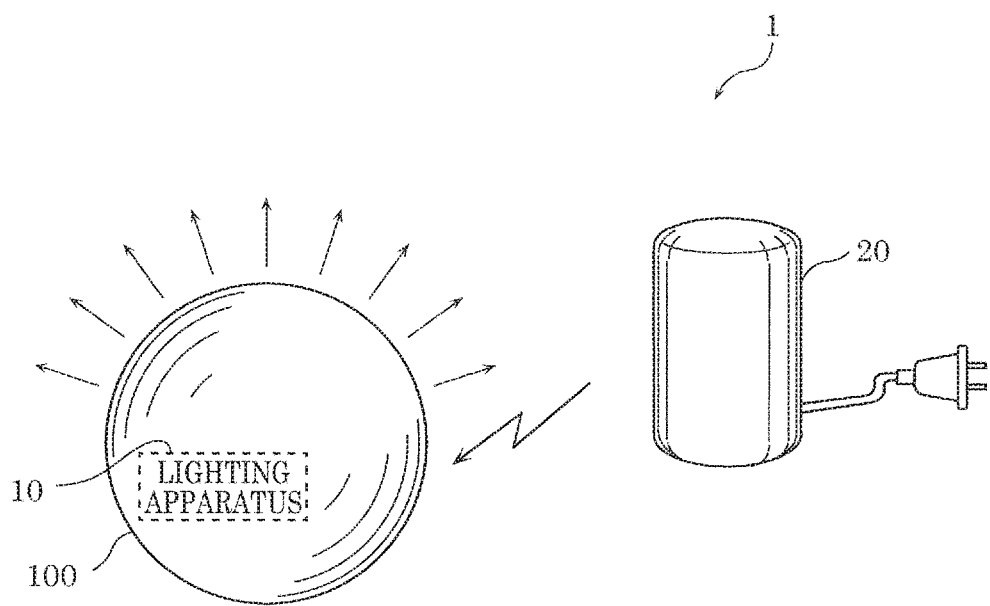
FIG. 1 is a diagram illustrating a configuration of a lighting system according to Embodiment 1.

Hereinafter, embodiments of the present disclosure are described. It is to be noted that each of the embodiments described below indicates an example of the present disclosure. Accordingly, the numerical values, constituent elements, the arrangement and connection of the constituent elements, steps, and the order of the steps etc. shown in the following exemplary embodiments are mere examples, and therefore do not limit the scope of the present disclosure. Therefore, among the constituent elements in the following exemplary embodiments, constituent elements not recited in any one of the independent claims that define the most generic inventive concept are described as arbitrary constituent elements.

Each diagram is a schematic diagram, and thus is not always precisely illustrated. It is to be noted that, in each diagram, substantially the same constituent elements are assigned the same reference numerals, and overlapping descriptions thereof are omitted or simplified.

Embodiment 1

[Lighting System]

Figure 2:
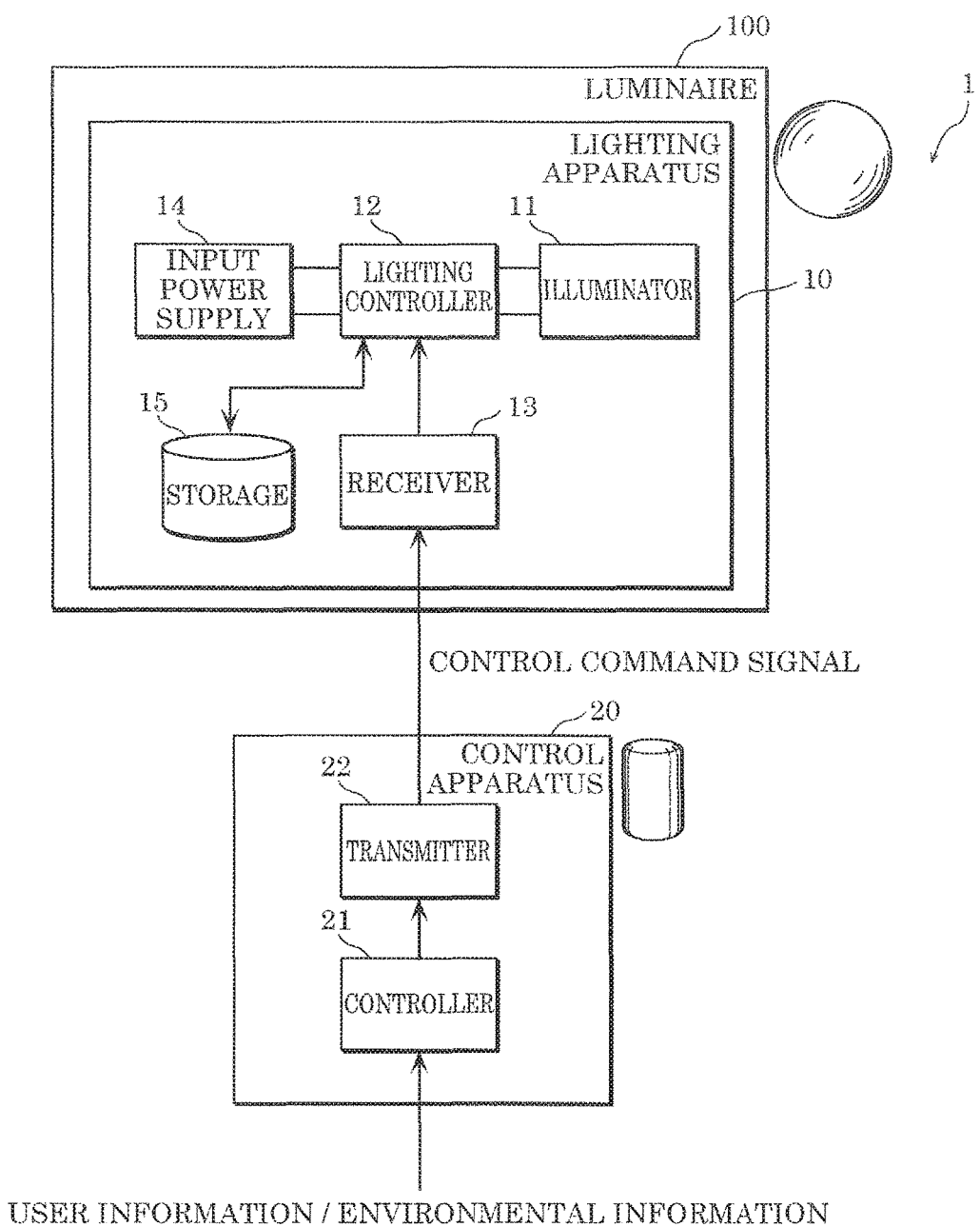
FIG. 2 is a block diagram illustrating a configuration of the lighting system according to Embodiment 1.

First, an example of lighting system 1 according to Embodiment 1 is described with reference to FIGS. 1 and 2. FIG. 1 is a diagram illustrating a configuration of lighting system 1 according to Embodiment 1. FIG. 2 is a block diagram illustrating a configuration of lighting system 1 according to Embodiment 1.

As illustrated in FIG. 1, lighting system 1 includes luminaire 100 and control apparatus 20. Lighting system 1 is used in, for example, a bedroom of a home. In this case, luminaire 100 and control apparatus 20 are provided in the bedroom. More specifically, luminaire 100 is disposed beside a bed so that a user is irradiated with illumination light even when the user is on the bed. It should be noted that the bedroom of the home is a mere example of a place at which lighting system 1 is disposed.

Luminaire 100 includes lighting apparatus 10 which emits illumination light, and is capable of emitting a desired illumination light by driving lighting apparatus 10. Luminaire 100 is, as a non-limiting example, a luminaire having a ball shape so as to emit illumination light omnidirectionally.

Control apparatus 20 is an apparatus for controlling luminaire 100. More specifically, control apparatus 20 controls illumination light to be emitted by luminaire 100.

Hereinafter, lighting apparatus 10 and control apparatus 20 are specifically described.

[Lighting Apparatus]

As illustrated in FIG. 2, lighting apparatus 10 embedded in luminaire 100 is a lighting apparatus which emits illumination light, and includes illuminator 11, lighting controller 12, receiver 13, input power supply 14, and storage 15.

Illuminator 11 includes light sources each of which emits illumination light. Illuminator 11 (light source) emits illumination light under predetermined illumination conditions. Predetermined illumination conditions include: conditions relating to an emission spectrum such as a brightness (illuminance), a light color, an average of rendering index (Ra); or conditions relating to time such as light emission start time, light emission end time, light emission duration time. In this embodiment, illuminator 11 emits white light as illumination light. It should be noted that the light source of illuminator 11 is an LED module including an LED. The LED emits light with a direct current power that is supplied from lighting controller 12. It should be noted that the LED is a non-limiting example of the light source of illuminator 11.

Illumination conditions of illumination light to be emitted by illuminator 11 are controlled by lighting controller 12. In other words, under the control of lighting controller 12, illuminator 11 changes a brightness or a color temperature and a light color etc. of illumination light to be emitted by illuminator 11. Illuminator 11 includes, as one or more light sources, a plurality of light sources which emit light having mutually different color temperatures. Accordingly, illuminator 11 has a dimming function for changing a brightness (output) of illumination light and a toning function for changing a color temperature and a light color of illumination light.

It should be noted that illumination conditions of illumination light to be emitted by illuminator 11 are not limited to conditions regarding an emission spectrum and time, and may be a light distribution angle etc. In this case, illuminator 11 may have a light distribution control function for changing a light distribution angle by automatically adjusting a lens disposed in illuminator 11, in addition to the dimming function and the toning function.

Lighting controller 12 controls illuminator 11. More specifically, lighting controller 12 controls light emission states of the light sources of illuminator 11. In this embodiment, lighting controller 12 changes illumination conditions of illumination light to be emitted by illuminator 11 (light sources) according to a control command signal received by receiver 13. For example, lighting controller 12 changes a brightness or a color temperature of illumination light to be emitted by illuminator 11 or changes timings for turning on and off illuminator 11.

Lighting controller 12 includes, for example, a driver circuit for driving the light sources of illuminator 11 in a desired manner according to the control command signal from receiver 13 and a processor etc. Examples of driver circuits include a control circuit and a power supply circuit. As an example of the processor, a micro processor unit (MPU) having a central processing unit (CPU) mounted thereon can be used.

Receiver 13 receives the control command signal for controlling illumination light to be emitted by illuminator 11 from control apparatus 20. The control command signal received by receiver 13 is output to lighting controller 12.

The control command signal received by receiver 13 is a signal for controlling illumination light. In this embodiment, the control command signal is generated based on at least one of user information and environmental information for controlling illumination light. More specifically, the control command signal is generated by control apparatus 20 based on the at least one of the user information and the environmental information. The control command signal is described in detail later.

Input power supply 14 is a power supply of lighting controller 12. For example, when luminaire 100 (lighting apparatus 10) can receive supply of power from a commercial alternating current power supply through an attachment plug (not illustrated) or the like, input power supply 14 may convert the alternating current power to direct current and supply the direct current power as input power to lighting controller 12, or input power supply 14 may supply the alternating current power itself as input power to lighting controller 12. When lighting controller 12 receives supply of alternating current power, lighting controller 12 converts the alternating current power to direct current power.

It should be noted that luminaire 100 (lighting apparatus 10) may receive power supply from control apparatus 20. In this case, control apparatus 20 generates direct current power, and supplies the direct current power as input power to luminaire 100 via a power supply line (not shown) which connects control apparatus 20 and luminaire 100.

Storage 15 stores in advance a plurality of illumination patterns for changing illumination light to be emitted by illuminator 11. For example, lighting controller 12 selects one illumination light control pattern from among the plurality of illumination patterns stored in storage 15, based on a control command signal received by receiver 13, and causes illuminator 11 to emit illumination light according to the selected control pattern. Specific examples of illumination light control patterns are described later. It should be noted that illumination patterns stored in storage 15 are not limited to those pre-stored in storage 15 at the time of shipment from a factory. For example, possible illumination patterns include: one generated based on newly obtained information such as a control command signal received by receiver 13 and added, or one obtained by modifying an illumination pattern pre-stored based on the newly obtained information.

In addition, storage 15 may further store other information, or a sequence of programs etc. necessary for processing performed by lighting apparatus 10. Storage 15 includes: a main memory device which is a non-volatile memory device such as an SRAM, a DRAM, etc. or an auxiliary memory device which is a non-volatile memory device such as a magnet disc, an optical disc, a magneto-optical disc, a semiconductor memory, etc.

[Control Apparatus]

Control apparatus 20 is an apparatus for controlling luminaire 100, and includes controller 21 and transmitter 22. More specifically, control apparatus 20 controls lighting apparatus 10 embedded in luminaire 100.

Controller 21 is configured with, for example, a system on a chip (SOC), and performs various kinds of control processes. In addition, controller 21 has an artificial intelligence (AI) embedded therein.

In this embodiment, controller 21 generates a control command signal for controlling illumination light to be emitted by luminaire 100 (lighting apparatus 10). More specifically, controller 21 automatically generates a desired control command signal using the AI, based on at least one of user information and environmental information. It should be noted that control apparatus 20 obtains in advance the user information and the environmental information before generating the control command signal.

User information is user-related data relating to a user who uses luminaire 100, and is, for example, physical feature data indicating a physical feature of the user, lifestyle data indicating a lifestyle of the user, activity amount data indicating the amount of activity of the user, vital data of the user, etc.

The physical feature data regarding the user indicates, for example, the age, sex, height, weight, or the like of the user. In addition, the lifestyle data regarding the user is information relating to the lifestyle of the user such as a get-up time and a bedtime. By means of the user inputting the physical feature data and lifestyle data regarding the user in advance in control apparatus 20 or luminaire 100, control apparatus 20 can obtain these data in advance. In addition, by the user transferring the physical feature data and lifestyle data which have been input in a mobile terminal such as a smartphone, control apparatus 20 may obtain the physical feature data and lifestyle data.

For example, when the user is awake, the activity amount data regarding the user indicates a degree of magnitudes of motions (an amount of activity) of the user, and is represented as an accumulation value of activity strengths and activity time. The activity amount data regarding the user can be measured as calories by a sensor such as an activity meter or the like. The activity amount data regarding the user may indicate the number of steps counted by a pedometer. The sensor which measures the data indicating the amounts of activity may be included in a wearable terminal worn by the user or in a mobile terminal such as a smartphone carried by the user. The activity amount data measured by the sensor is transferred to control apparatus 20.

In addition, the activity amount data regarding the user when the user is on the bed (during a sleep) is body movement data indicating body movements of the user. The body movement data regarding the user can be measured using a body movement sensor such as a Doppler sensor. The body movement sensor is disposed on the bed used by the user. The activity amount data measured by the body movement sensor is transferred to control apparatus 20.

The vital data regarding the user include a pulse (a heart rate), a body temperature, a blood pressure, a brain wave, etc. Such vital data can be measured by various kinds of sensors. For example, a pulse, a body temperature, a blood pressure, and a brain wave can be measured by a pulse sensor, a thermometer, a blood pressure meter, and a brain wave meter, respectively. The sensors which measure these vital data may be included in wearable terminals worn by the user, in meters used by the user in the measurement, or in a mobile terminal such as a smartphone owned by the user. The vital data measured by these sensors are transferred to control apparatus 20.

Environmental information relates to, for example, an environment around luminaire 100 such as data relating to a weather, air quality, brightness, or/and the like. It should be noted that the environmental information may be environmental data regarding an environment of the user when the user is outside of his or her home. The environmental data can be measured by various kinds of environment sensors.

Weather data include an air temperature, a humidity, and an air pressure etc. which can be measured by a thermometer, a hydrometer, and a barometer etc., respectively. The air quality data relates to, for example, particles such as dust, pollen, smoke, and PM 2.5 and the concentration of gas such as carbon dioxide can be measured by a particle sensor and a gas concentration sensor, respectively. The brightness data can be measured by an illuminance sensor.

In this way, the user information and the environmental information as sensor information can be obtained by various kinds of sensors or by means of being input in control apparatus 20 or the like in advance. When the user information and the environmental information as the sensor information is obtained, sensors for obtaining the sensor information may be included in control apparatus 20 itself or included in any of various kinds of apparatuses such as wearable terminals and smartphones represented as the above sensor apparatus which is a pre-stage apparatus for controller 20. When the pre-stage apparatus includes the sensor, by means of the sensor information obtained by the pre-stage apparatus being transmitted to controller 20, control apparatus 20 can automatically obtain the sensor information as described above. In other words, in this case, control apparatus 20 receives the sensor information transmitted from the pre-stage apparatus including the sensor, automatically calculates illumination light suitable for the user and the environment based on the sensor information using an artificial intelligence (AI) of controller 21, and generates a control command signal for causing illuminator 11 to emit illumination light suitable for the user and the environment.

It should be noted that methods for obtaining the various kinds of information such as the user information and the environmental information are not limited to the above obtaining methods. For example, user information and environmental information may be fully automatically obtained irrespective of whether the user intends to obtain the information.

In this embodiment, when control apparatus 20 generates a control command signal, the AI of controller 21 automatically determines an illumination mode for emission of illumination light which is desired by the user, based on the user information and the environmental information obtained by the sensor, and selects the control command information corresponding to the determined illumination mode. Specific examples of illumination modes and control command signals corresponding to the illumination modes are described later.

It should be noted that control apparatus 20 may automatically obtain user information and environmental information from a cloud server instead of obtaining the user information and environmental information from the sensor. In this case, the user information obtained by a wearable terminal or a mobile terminal such as a smartphone owned by the user or environmental information obtained by an environmental sensor are transmitted to a cloud server so that the user information and environmental information are accumulated in the cloud server. In addition, control apparatus 20 automatically calculates illumination light suitable for the user and the environment using the AI of controller 21, based on the user information and the environmental information accumulated in the cloud server, to generate a desired control command.

Transmitter 22 transmits the control command signal generated by controller 21 to luminaire 100 (lighting apparatus 10). More specifically, transmitter 22 transmits the control command signal to receiver 13 of luminaire 10. Transmission from transmitter 22 to receiver 13 may be performed in any of a wired and wireless manner.

It should be noted that control apparatus 20 may include a power supply (power supply circuit) etc. in addition to controller 21 and transmitter 22. For example, the power supply receives supply of commercial alternating current power through an attachment plug.

[Control Command Signal]

Here, control command signals which control apparatus 20 transmits to luminaire 100 (lighting apparatus 10) are described with reference to FIG. 3. FIG. 3 is a diagram illustrating examples of control command signals for use by lighting system 1 according to Embodiment 1.

Each control command signal includes one or more parameters including, as an element, at least one of a brightness of illumination light, a color temperature of the illumination light, and control time for controlling the illumination light. In other words, at least one of the brightness, color temperature, and control time of the illumination light to be emitted by illuminator 11 is included as the element in each parameter of the control command signal.

More specifically, in this embodiment, six control command signals are used as illustrated in FIG. 3, and each control command signal includes one or more parameters.

Control command signal A1 indicating "a turn-on signal" is a signal for causing illuminator 11 to start an ON state. Control command signal A1 includes: a first parameter indicating a brightness of illumination light which is emitted by illuminator 11; a second parameter indicating a color temperature of the illumination light which is emitted by illuminator 11; and a third parameter indicating control time for controlling the illumination light which is emitted by illuminator 11. In control command signal A1 as a non-limiting example, the first parameter (brightness), the second parameter (color temperature), and the third parameter (control time) have a range from 5% to 100%, a range from 2000 K to 6500 K, and a range from 0 to 200×0.1 [s], respectively.

Control command signal A2 indicating "an up/down signal" is a signal for changing at least one of the brightness and color temperature of illumination light to be emitted by illuminator 11. Likewise control command signal A1, control command signal A2 includes: a first parameter indicating a brightness of illumination light which is emitted by illuminator 11; a second parameter indicating a color temperature of the illumination light which is emitted by illuminator 11; and a third parameter indicating control time for controlling the illumination light which is emitted by illuminator 11. In control command signal A2 as a non-limiting example, the first parameter (brightness), the second parameter (color temperature), and the third parameter (control time) have a range from 5% to 100%, a range from 2000 K to 6500 K, and a range from 0 to 120×0.5 [s], respectively.

Control command signal A3 indicating "a turn-off signal" is a signal for causing illuminator 11 to end an ON state. Control command signal A3 is composed only of a first parameter indicating control time that lasts until illuminator 11 is caused to stop emitting illumination light. In control command signal A3 as a non-limiting example, the first parameter (control time) has a range from 0 to 200×0.1 [s].

Control command signal B1 indicating "a light alarm signal" is a signal for causing illuminator 11 to turn on in a light alarm mode. The light alarm mode is a mode for waking up a user on the bed by gradually increasing brightness of illumination light which is being emitted by illuminator 11. Control command signal B1 includes: a first parameter indicating control time for controlling illumination light which is emitted by illuminator 11; and a second parameter indicating a brightness of the illumination light which is emitted by illuminator 11. In control command signal B1 as a non-limiting example, the first parameter (control time) and the second parameter (brightness) have a range from 10 to 30×1 [min] and a range from 5% to 100%, respectively.

Control command signal C1 indicating "a light alert signal" is a signal for causing illuminator 11 to turn on in light alert mode. The light alert mode is a mode for notifying the user that a predetermined control target apparatus will start to operate soon, by changing the brightness of illumination light which is being emitted by illuminator 11. Control command signal C1 includes: a first parameter indicating an interval of emission of illumination light by illuminator 11 in a light alert mode; and a second parameter indicating the number of times of emission of illumination light by illuminator 11 in a light alert mode. In control command signal C1 as a non-limiting example, the first parameter (interval) and the second parameter (the number of times) have a range from 10 to 30×1 [min] and a range from 1 to 5 [time(s)], respectively.

It should be noted that, in control command signal C1, the first parameter (indicating the interval) includes all elements of the brightness of illumination light emitted by illuminator 11, the color temperature of the illumination light emitted by illuminator 11, and the control time for controlling the illumination light.

Control command signal D1 indicating "a fluctuation signal" is a signal for causing illuminator 11 to turn on in a fluctuation mode. The fluctuation mode is a mode for alternately repeating a mode for increasing a brightness of illumination light which is being emitted by illuminator 11 and a mode for decreasing a brightness of illumination light which is being emitted by illuminator 11. Control command signal D1 includes: a first parameter indicating control time for controlling the illumination light which is emitted by illuminator 11; a second parameter indicating a brightness of the illumination light which is emitted by illuminator 11; and a third parameter indicating a color temperature of the illumination light which is emitted by illuminator 11. In control command signal D1 as a non-limiting example, the first parameter (control time), the second parameter (brightness), and the third parameter (color temperature) have a range from 0 to 10×1 [min], a range from 0% to 50%, and a range from 2000 K to 6500 K, respectively.

In this embodiment, each of the control command signals including a plurality of parameters among the six control command signals collectively includes all of the plurality of single control command signals to be transmitted in a single transmission. More specifically, each of control command signal A1, control command signal A2, and control command signal D1 collectively includes the first parameter, the second parameter, and the third parameter to be transmitted in the single transmission. Each of control command signal B1 and control command signal C1 collectively includes the first parameter and the second parameter to be transmitted in a single transmission.

It is to be noted that the first parameter, the second parameter, and the third parameter in each control command signal may be processed by lighting controller 12 as parameters prioritized in this order.

[State Transitions of Lighting Apparatus]

Figure 4:
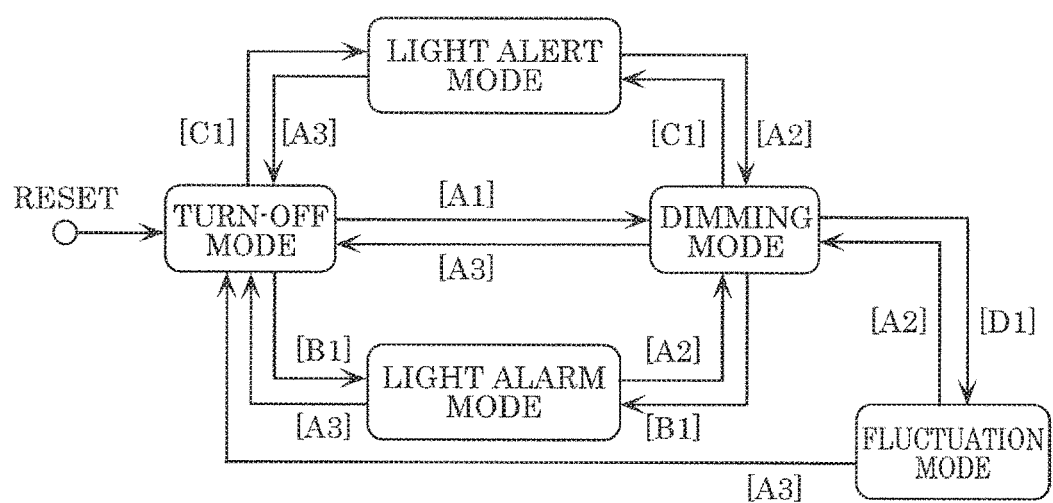
FIG. 4 is a diagram illustrating state transitions of a luminaire according to Embodiment 1.

Next, state transitions of luminaire 100 (lighting apparatus 10) according to this embodiment are described with reference to FIG. 4. FIG. 4 is a diagram illustrating state transitions of luminaire 100 according to this embodiment.

An illumination mode of luminaire 100 (lighting apparatus 10) transits when a control command signal is transmitted from control apparatus 20. In other words, the illumination mode transits upon receiver 13 receiving the control command signal.

As illustrated in FIG. 4, luminaire 100 (lighting apparatus 10) has the following illumination modes: a turn-off mode; a dimming mode; a fluctuation mode; a light alarm mode (ASSA mode); and a light alert mode.

In each illumination mode, a light emission state of illuminator 11 is controlled by means of lighting controller 12 processing a control command signal received by receiver 13. In this case, for example, lighting controller 12 changes a first set value (current value) indicating one of a brightness and a color temperature of illumination light that is being emitted by illuminator 11 to a second set value (target value) indicating one of a brightness and a color temperature indicated in a current control command signal. At this time, lighting controller 12 changes the current value of the one of the brightness and the color temperature of the illumination light emitted by illuminator 11 while changing the first set value to the second set value. In other words, a trajectory to the target value for illumination light may change with time.

At this time, the number of control patterns for changing illumination light having a first set value to illumination light having a second set value may be two or more. In other words, a trajectory to the target value for illumination light may be produced according to a plurality of control patterns. For example, the plurality of control patterns are stored in storage 15 of lighting apparatus 10. In this case, lighting controller 12 selects one control pattern from among the two or more control patterns stored in storage 15 according to a current control command signal, and changes the first set value to the second set value according to the selected control pattern.

Hereinafter, descriptions are given of specific examples of control patterns for illumination light which is emitted by illuminator 11 in respective illumination modes.

When receiver 13 receives control command signal A3 indicating "a turn-off signal", lighting controller 12 controls illumination light to be emitted by illuminator 11 (light source) according to a turn-off mode. The turn-off mode is a mode for causing illuminator 11 to turn off. In the turn-off mode, a dimming signal such as a PWM signal becomes 0, and illuminator 11 (light source) turns off.

When receiver 13 receives control command signal A2 indicating "an up/down signal", lighting controller 12 controls illumination light to be emitted by illuminator 11 (light source) according to a dimming mode. The dimming mode is a dimming and toning mode for changing at least one of a brightness of illumination light to be emitted by illuminator 11 (light source) and a color temperature of the illumination light to be emitted by illuminator 11 (light source). In this embodiment, toning is performed by performing dimming. In the dimming mode, dimming control is started based on a control command signal.

Figure 5:
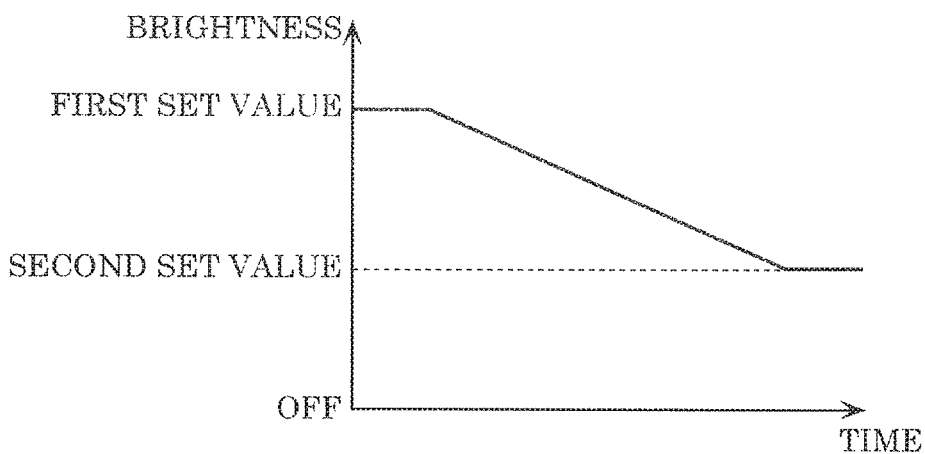
FIG. 5 is a diagram illustrating an example of an illumination light control pattern in a dimming mode of the luminaire according to Embodiment 1.
Figure 6:
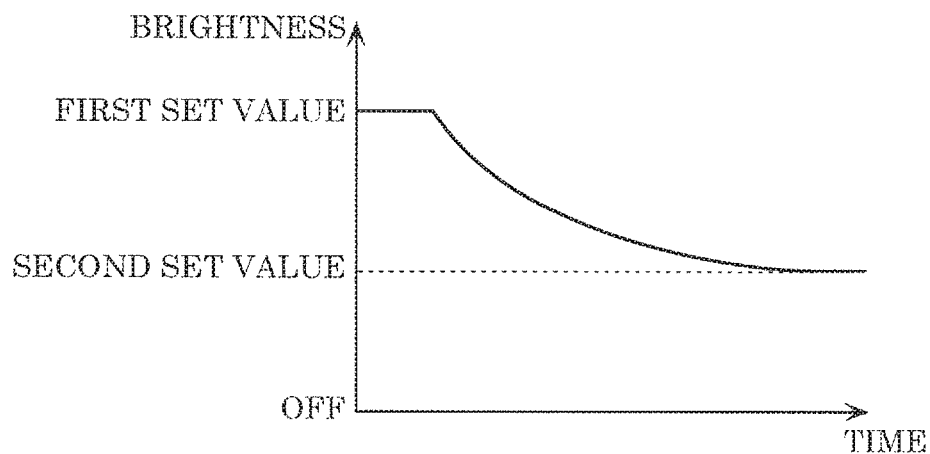
FIG. 6 is a diagram illustrating another example of an illumination light control pattern in a dimming mode of the luminaire according to Embodiment 1.

Control patterns for illumination light in a dimming mode may be: a dimming control pattern for linearly decreasing the brightness of illumination light which is emitted by illuminator 11; or a dimming control for quadratically decreasing the brightness of illumination light which is emitted by illuminator 11. In the example of each of FIGS. 5 and 6, the first set value is a dimming rate of 100% and the second set value is a dimming rate of 50%. It should be noted that control patterns in a dimming mode may be dimming control patterns for increasing brightness of illumination light which is emitted by illuminator 11.

When receiver 13 receives control command signal B1 indicating "a light alarm signal", lighting controller 12 controls illumination light which is emitted by illuminator 11 in a light alarm mode. The light alarm mode is a mode for gradually increasing the brightness of illumination light which is emitted by illuminator 11 (light source). In the light alarm mode, target dimming steps are calculated based on a control command signal. Although the color temperature is constant at 2000 K in the light alarm mode, it should be noted that 2000 K is a non-limiting example.

Figure 7:
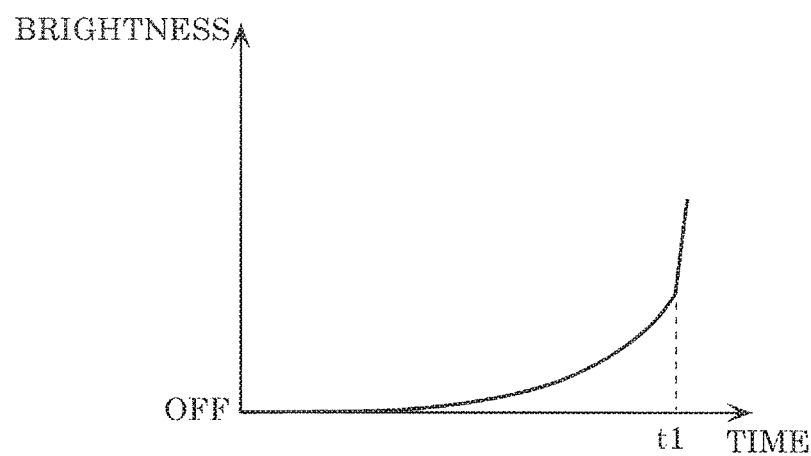
FIG. 7 is a diagram illustrating an example of an illumination light control pattern in a light alarm mode of the luminaire according to Embodiment 1.

The control pattern of illumination light in the light alarm mode is, for example, a pattern for performing a light alarm control for gradually increasing the brightness of illumination light which is emitted by illuminator 11, as illustrated in FIG. 7. In addition, as illustrated in FIG. 7, boost control for drastically changing the brightness of illumination light which is being emitted by illuminator 11 may be performed in the latter part (for example, at t1 in FIG. 7) of the light alarm control. In this case, the boost control can be performed by performing dimming control for changing at least one of the brightness of the illumination light and the color temperature of the illumination light. In this way, since control command signal B1 includes a temporal element in the parameters, it is also possible to perform a dimming control in which the boost control is performed according to single control command signal B1. It should be noted that control patterns in the light alarm mode are not limited to the patterns illustrated in FIG. 7.

When receiver 13 receives control command signal C1 indicating "a light alert signal", lighting controller 12 controls illumination light which is emitted by illuminator 11 in a light alert mode. The light alert mode is a mode for notifying the user that a predetermined control target apparatus will start to operate soon, by changing the brightness of illumination light which is being emitted by illuminator 11 (light source). In the light alert mode, an initial light emission state is held, and the timing for changing the initial light emission state based on a control command signal is determined, and then dimming control is performed. After the control of the illumination light in the light alert mode is finished, a return to the held initial light emission state is made.

Control patterns of illumination light in the light alert mode is, for example, a pattern for performing a light alert control for changing the brightness of illumination light which is emitted by illuminator 11, thereby notifying the user that a predetermined control target apparatus will start to operate soon. It should be noted that specific examples of control patterns of illumination light in the light alert mode are described in detail in Embodiment 2.

When receiver 13 receives control command signal D1 indicating "a fluctuation signal", lighting controller 12 controls illumination light which is emitted by illuminator 11 in a fluctuation mode. The fluctuation mode is a mode for alternately repeating a state in which the brightness of illumination light which is emitted by illuminator 11 (light source) is increased and a state in which the brightness of illumination light which is emitted by illuminator 11 (light source) is decreased. In the fluctuation mode, program steps are calculated based on a control command signal, and dimming control is performed.

Figure 8:
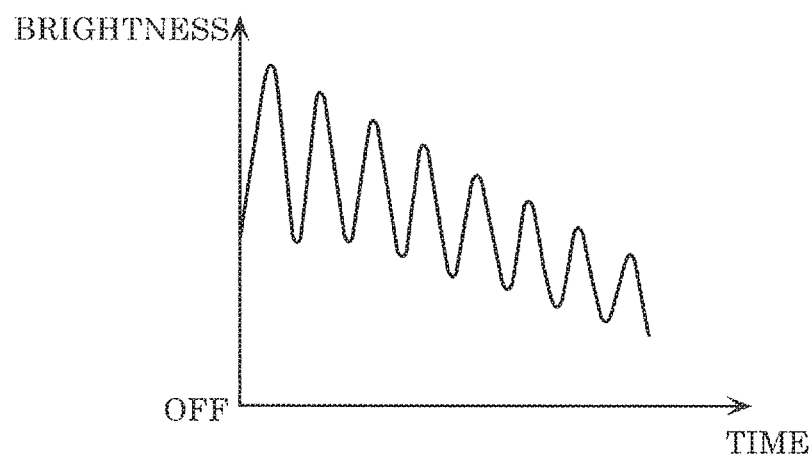
FIG. 8 is a diagram illustrating an example of an illumination light control pattern in a fluctuation mode of the luminaire according to Embodiment 1.

Control patterns of illumination light in the fluctuation mode are, for example, patterns for performing a fluctuation control for alternately repeating the mode for increasing the brightness of illumination light to be emitted by illuminator 11 and the mode for decreasing the brightness of illumination light to be emitted by illuminator 11, as illustrated in FIG. 8. It should be noted that control patterns in the fluctuation mode are not limited to the patterns illustrated in FIG. 8.

The plurality of illumination modes (light emission states) of luminaire 100 transit as described below.

When luminaire 100 (lighting apparatus 10) is turned on, a reset state thereof transits to a turn-off mode.

When receiver 13 receives control command signal A1, B1, or C1 in a turn-off mode, the turn-off mode of luminaire 100 transits to one of a dimming mode, a light alarm mode, and a light alert mode, respectively.

When receiver 13 receives control command signal B1, C1, D1, or A3 in a dimming mode, the dimming mode of luminaire 100 transits to one of a light alarm mode, a light alert mode, a fluctuation mode, and a turn-off mode, respectively.

When receiver 13 receives control command signal A2 or A3 in a light alarm mode, the light alarm mode of luminaire 100 transits to one of a dimming mode and a turn-off mode, respectively.

When receiver 13 receives control command signal A2 or A3 in a light alert mode, the light alert mode of luminaire 100 transits to one of a dimming mode and a turn-off mode, respectively.

In this way, in luminaire 100, transitions to the light alarm mode, the light alert mode, and the fluctuation mode are made from the dimming mode (starting point). More specifically, transitions from the light alarm mode, the light alert mode, and the fluctuation mode are made only to one of the dimming mode and the turn-off mode.

It should be noted that a state for waiting a next control command signal is created in each of the illumination modes. When receiver 13 received the next control command signal, the light emission state of illuminator 11 is controlled in the illumination mode based on the latest control command signal.

CONCLUSION

As described above, lighting apparatus 10 according to this embodiment includes: illuminator 11 including the light sources which emit illumination light; lighting controller 12 which controls illuminator 11; and receiver 13 which receives, from control apparatus 20 (another apparatus/the other apparatus), a control command signal generated based on at least one of the user information and the environmental information in order to control illumination light. The control command signal received by receiver 13 includes the one or more parameters including, as the element, the at least one of the brightness of the illumination light, the color temperature of the illumination light, and the control time for controlling the illumination light.

In this way, except for the initial settings, it is possible to cause lighting apparatus 10 to automatically emit illumination light suitable for the user and the environment without the need for the user to operate lighting apparatus 10. More specifically, lighting apparatus 10 is capable of automatically controlling such illumination light to be emitted by illuminator 11 only by receiving the control command signal from control apparatus 20, without the need for the user to operate lighting apparatus 10 via a remote controller so as to change illumination light from illuminator 11.

In lighting apparatus 10 according to this embodiment, receiver 13 receives the control command signal which has been generated by control apparatus 20 based on the at least one of the user information and the environmental information which has been obtained by the sensor as the sensor information. In this case, control apparatus 20 may receive the sensor information transmitted from the apparatus including the sensor as the user information and the environmental information.

In this way, by means of the sensor obtaining the user information and the environmental information, control apparatus 20 is capable of automatically generating the control command signal based on the at least one of the obtained user information and the environmental information. In other words, it is possible to automatically obtain the user information and environmental information and generate the control command signal without any user operation. Accordingly, it is possible to easily cause illuminator 11 to emit illumination light suitable for the user and the environment without the need of any user operation.

It should be noted that the user information and the environmental information may be obtained from a cloud server instead of the sensor. In this case, receiver 13 receives the control command signal generated by control apparatus 20 based on the user information and the environmental information accumulated in the cloud server.

In this way, it is possible to easily cause the emission of the illumination light suitable for the user and the environment without the need of any user operation by also obtaining the user information and the environmental information from the cloud server.

In lighting apparatus 10 according to this embodiment, the plurality of parameters which constitute the given control command signal are the first parameter indicating the brightness of the illumination light, the second parameter indicating the color temperature of the illumination light; and the third parameter indicating the control time for controlling the illumination time.

In this way, it is possible to easily cause illuminator 11 to emit the desired illumination light based on the parameters indicating the brightness and color temperature of the illumination light, and the control time for controlling the illumination light.

In this case, likewise control command signal A1 indicating "a turn-on signal", control command signal A2 indicating "an up/down signal", and control command signal D1 indicating "a fluctuation signal", a control command signal may collectively include the first parameter, the second parameter, and the third parameter to be transmitted in a single transmission.

Alternatively, likewise the first parameter in control command signal C1 indicating "a light alert signal", one parameter may include all the elements which are the brightness and color temperature of illumination light, and the control time for controlling the illumination light.

In addition, as illustrated in FIG. 4, lighting apparatus 10 according to this embodiment has illumination modes of: the turn-off mode, the dimming mode, the light alarm mode, the light alert mode, and the fluctuation mode.

Figure 9:
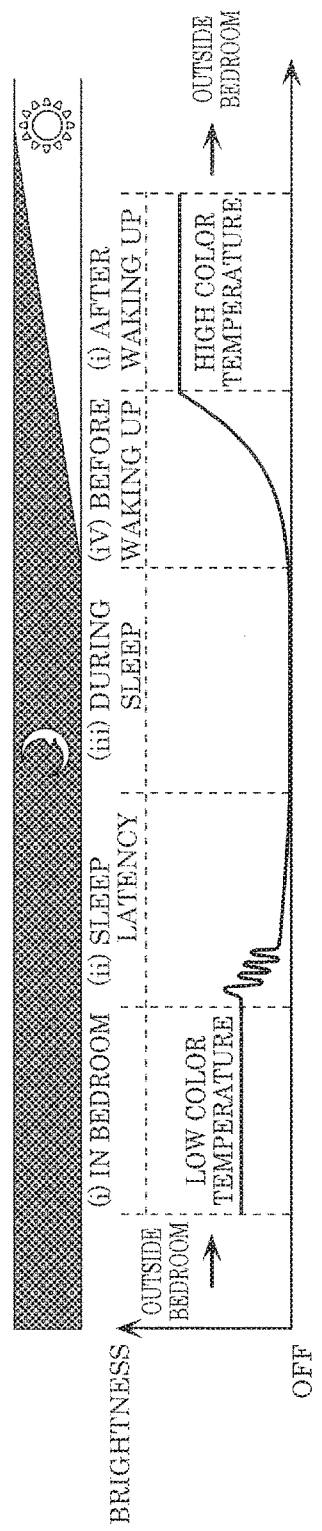
FIG. 9 is a diagram illustrating a use example of the lighting system according to Embodiment 1.

In this way, lighting apparatus 10 is capable of performing sleeping support (for sleeping, getting up, etc.) as illustrated in FIG. 9.

For example, when the user is in a bedroom before going to bed, illuminator 11 is controlled in the dimming mode in which lighting apparatus 10 is controlled to turn on and emit illumination light having a relaxing low color temperature and to turn on and emit illumination light which adjusts a wake-up rhythm.

In sleep latency, illuminator 11 is controlled in the fluctuation mode in order to induce the user into a comfortable sleep, so that lighting apparatus 10 can emit illumination light which allows the user to fall into a comfortable sleep.

During a sleep, lighting apparatus 10 is set to the turn-off mode so as to turn off illuminator 11. At this time, for example, a body movement of the user is sensed by the sensor, and when it is determined that the user has just fallen asleep, lighting apparatus 10 is automatically set to the turn-off mode.

Before the user wakes up, illuminator 11 is controlled in the light alarm mode in order to induce the user into a light sleep, so that the color temperature of illumination light which is emitted by illuminator 11 is changed from low to high and the brightness of the illumination light is gradually increased.

After the user wakes up, in order to cause the user to get up pleasantly, illuminator 11 is controlled in the turn-on mode or the dimming mode, so as to cause lighting apparatus 10 to emit illumination light having a high color temperature for fully waking up the user.

Embodiment 2

Figure 10:
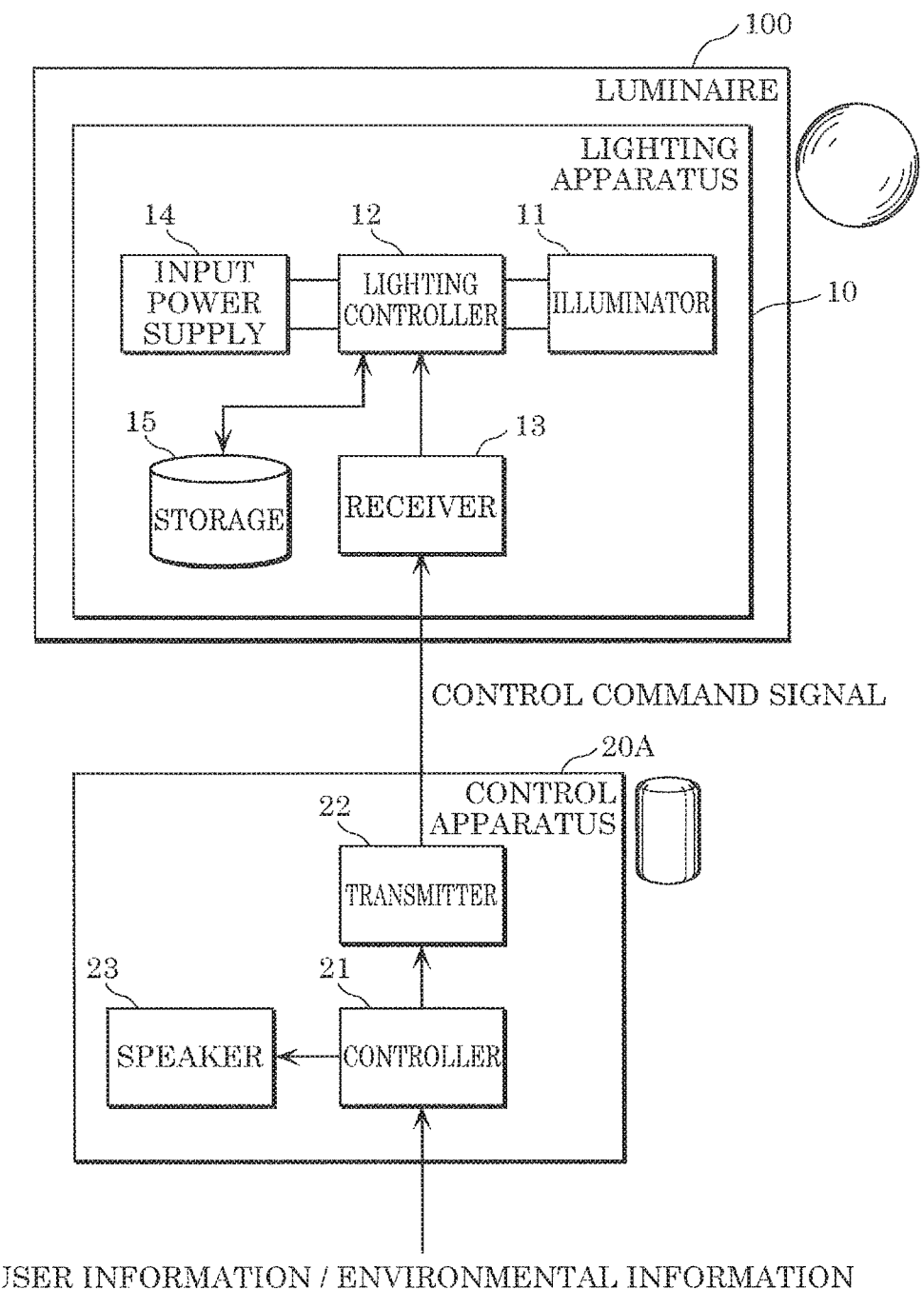
FIG. 10 is a block diagram illustrating a configuration of the lighting system according to Embodiment 2.

Next, a lighting system according to Embodiment 2 is described. FIG. 10 is a block diagram illustrating a configuration of the lighting system according to Embodiment 2.

Likewise lighting system 1 according to Embodiment 1, the lighting system according to this embodiment includes: luminaire 100 including lighting apparatus 10; and control apparatus 20A which controls luminaire 100 (lighting apparatus 10).

As in Embodiment 1, lighting apparatus 10 includes: illuminator 11; lighting controller 12; receiver 13; input power supply 14; and storage 15.

As in Embodiment 1, control apparatus 20A includes controller 21 and transmitter 22. Control apparatus 20A according to this embodiment further includes speaker 23. Speaker 23 notifies sound information such as music around control apparatus 20A.

In this embodiment, lighting apparatus 10 and control apparatus 20A are respectively configured to have the same functions as in Embodiment 1.

Accordingly, also in luminaire 100 (lighting apparatus 10) according to this embodiment, when receiver 13 receives a control command signal transmitted from control apparatus 20A, lighting controller 12 controls illumination light emitted by illuminator 11 according to the control command signal.

In addition, in this embodiment, luminaire 100 (lighting apparatus 10) has, as lighting modes, a turn-off mode under turn-off control, a dimming mode under dimming control, a fluctuation mode under fluctuation control, a light alarm mode under light alarm control, and a light alert mode under light alert mode, one of which transits to a predetermined lighting mode according to the control command among the other lighting modes.

Figure 11:
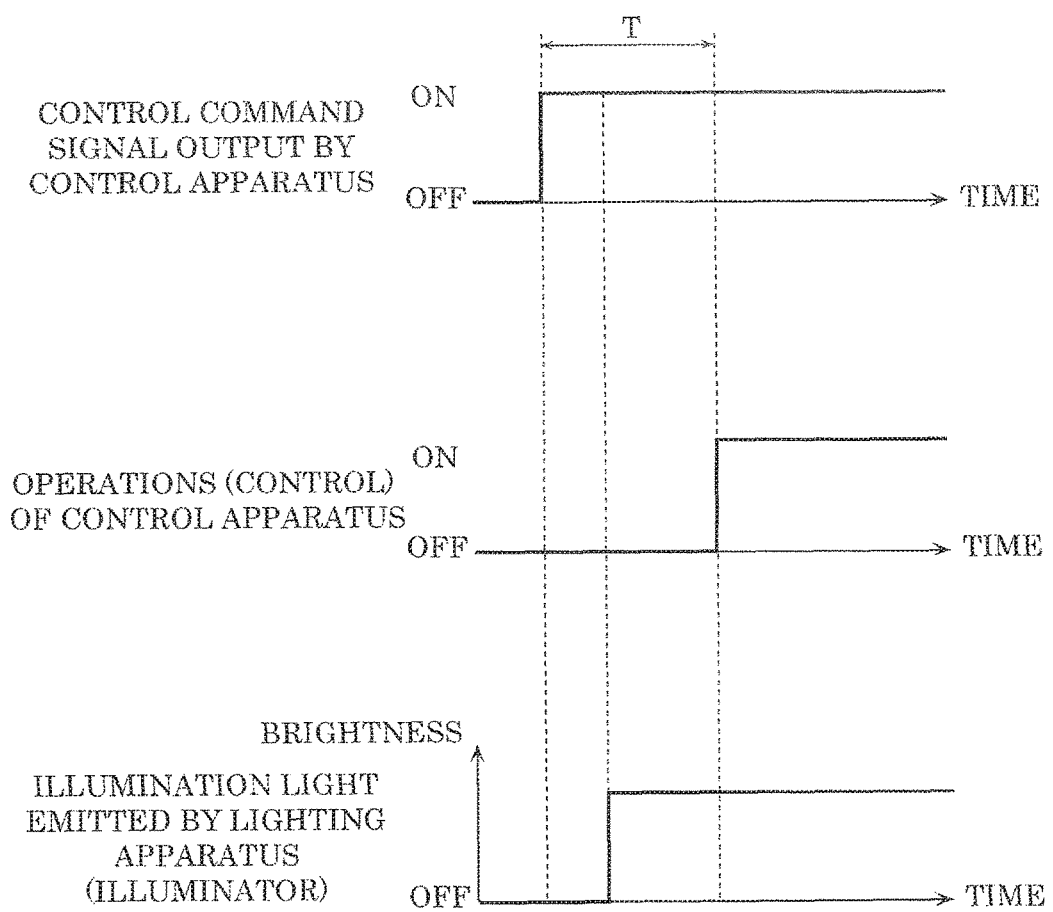
FIG. 11 is a diagram illustrating a first example of control performed by the luminaire and control performed by a control apparatus according to Embodiment 2.

This embodiment is particularly characterized by the light alert control in the light alert mode. Hereinafter, a specific example of the light alert control according to this embodiment is described using FIG. 11 with reference to FIG. 10. FIG. 11 is a diagram illustrating an example of control performed by lighting apparatus 10 and control performed by control apparatus 20A according to Embodiment 2.

As illustrated in FIG. 11, in luminaire 100 (lighting apparatus 10) according to this embodiment, when receiver 13 has received a control command signal from control apparatus 20A, lighting controller 12 changes the brightness of illumination light to be emitted by illuminator 11 by performing light alert control on illuminator 11 before a control target apparatus different from lighting apparatus 10 starts to operate (under control).

In this embodiment, the control target apparatus is control apparatus 20A. More specifically, when receiver 13 of lighting apparatus 10 receives the control command signal from controller 20A, the brightness of illumination light that is being emitted by illuminator 11 is changed before control apparatus 20A starts to operate (for example, to reproduce music).

More specifically, first, controller 21 of control apparatus 20A generates the control command signal based on at least one of user information and environmental information. The generated control command signal is transmitted from transmitter 22 to luminaire 100 (lighting apparatus 10).

When lighting apparatus 10 receives the control command signal from control apparatus 20A, lighting controller 12 changes the brightness of illumination light emitted by illuminator 11 before control apparatus 20A starts to operate. For example, when receiver 13 receives control command signal A1 indicating "a turn-on signal" from control apparatus 20A, illuminator 11 turns on before control apparatus 20A starts to operate.

After the brightness of illumination light emitted by illuminator 11 is changed, control apparatus 20A starts to operate. More specifically, when predetermined period T elapsed after control apparatus 20A transmitted a control command signal, control apparatus 20A starts to operate. For example, reproduction of music is started and the music is notified through speaker 23.

Predetermined period T is a period in which control apparatus 20A is prevented from operating. It is to be noted that, in this embodiment, predetermined period T (an operation prohibition period) may be preset in control apparatus 20A and be included in a control command signal. In other words, predetermined period T is determined by control apparatus 20A.

In this way, in this embodiment, control apparatus 20A is prevented from starting to operate during the period (predetermined period T) from when control apparatus 20A transmits the control command signal to when the brightness of illumination light that is being emitted by illuminator 11 changes. Thus, the brightness of illumination light emitted by illuminator 11 changes before control apparatus 20A starts to operate. In other words, the start of the operation of control apparatus 20A is notified to the user by changing the brightness of illumination light emitted by illuminator 11.

In this way, the user can expect in advance that control apparatus 20A will start to operate soon, and thus can be ready for the start of the operation of control apparatus 20A. For example, the user can expect that music will be reproduced soon. Accordingly, it is possible to reduce the psychological burden of the user caused by an abrupt operation of control apparatus 20A, and to notify the user that control apparatus 20A will start to operate soon, by providing a small stimulus.

Figure 12:
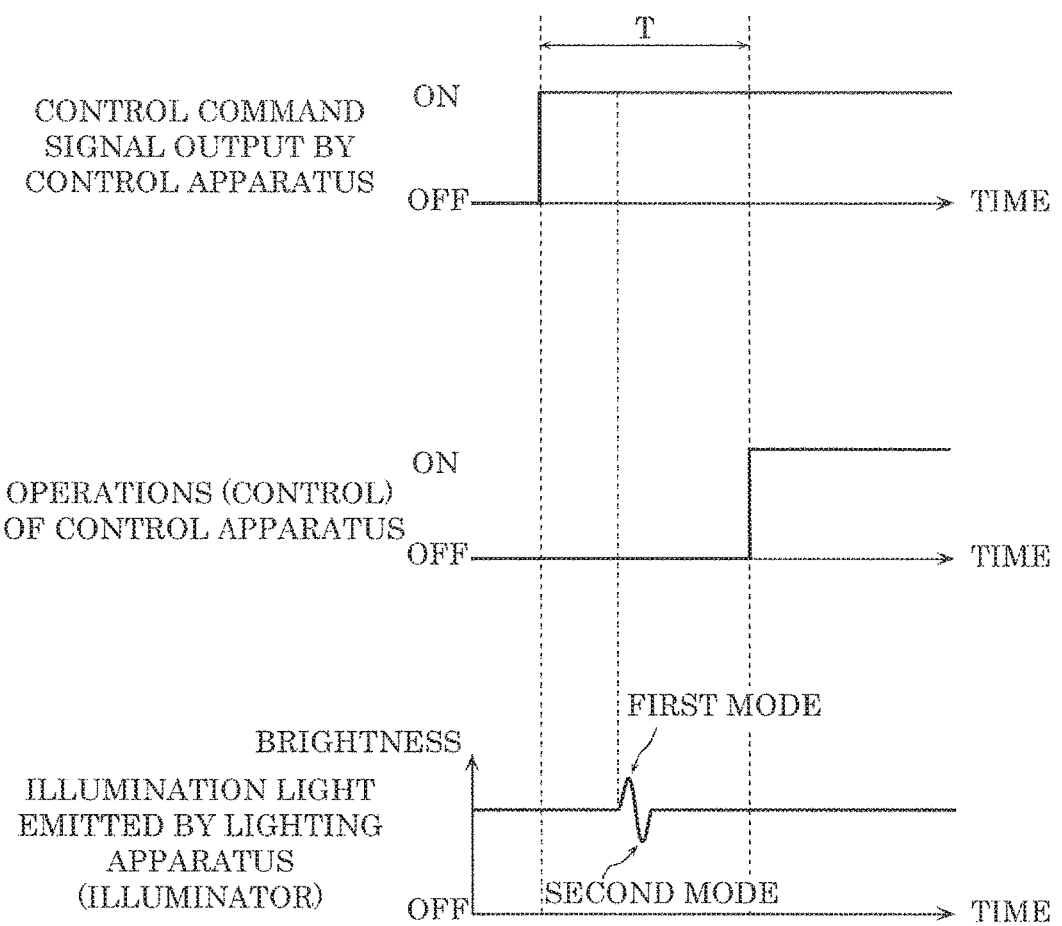
FIG. 12 is a diagram illustrating a second example of control performed by the luminaire and control performed by the control apparatus according to Embodiment 2.

In addition, patterns of illumination light under light alert control are not limited to the pattern illustrated in FIG. 11, and may be a pattern illustrated in FIG. 12.

In FIG. 12, when receiver 13 receives a control command signal, lighting controller 12 performs light alert control on illuminator 11 so that transitions to a first mode for increasing the brightness of illumination light to be emitted by illuminator 11 and a second mode for decreasing the brightness of illumination light to be lower than the brightness of illumination light in the first mode are made in sequence, and then the state of illuminator 11 returns to the state before the control command signal is received.

More specifically, in the first mode, the illumination light changes in a curved waveform such that the brightness at the start time of reception of the control command signal is gradually increased and then returns to the brightness at the start time, and in the second mode next to the first mode, the illumination light changes in a curved waveform such that the brightness at the start time of reception of the control command signal is gradually decreased and then returns to the brightness at the start time.

In this way, with the repetition of the first mode for increasing the brightness with respect to the brightness at the start time of the reception of the control command signal and the second mode for decreasing the brightness with respect to the brightness at the start time of the reception of the control command signal, the user easily feels the difference in brightness of the illumination light. In this way, the user easily recognizes the change in brightness of the illumination light emitted by illuminator 11. In addition, as illustrated in FIG. 12, changing the illumination light in the curved waveform makes it possible to notify the user that control apparatus 20A will start to operate soon, by providing a pleasant stimulus. Furthermore, since the brightness is increased first by performing the second mode before the first mode, the user recognizes the change in brightness of the illumination light more easily than in the case where the brightness is decreased first (from the second mode to the first mode).

Furthermore, by repeating the first mode for increasing the brightness based on a reference brightness that is the brightness at the time of reception of the control command signal and the second mode for decreasing the brightness based on the reference brightness, it is possible to cause the user to recognize the change in brightness of the illumination light by providing a stimulus gentler than those in the case of only increasing (or only decreasing) the brightness based on the reference brightness even if the difference in brightness is the same as those in the case.

In addition, when performing light alert control by repeating the first mode and the second mode, it is beneficial that lighting controller 12 controls illuminator 11 such that the color temperature of illumination light in the first mode is higher than the color temperature of illumination light in the second mode.

In this way, it is possible to cause the user to recognize the change in brightness of the illumination light more easily by providing a small stimulus.

In this case, it is good that lighting controller 12 controls illuminator 11 such that the color temperature of illumination light changes gradually.

In this way, it is possible to cause the user to recognize the change in brightness of the illumination light by providing a smaller stimulus.

Figure 13:
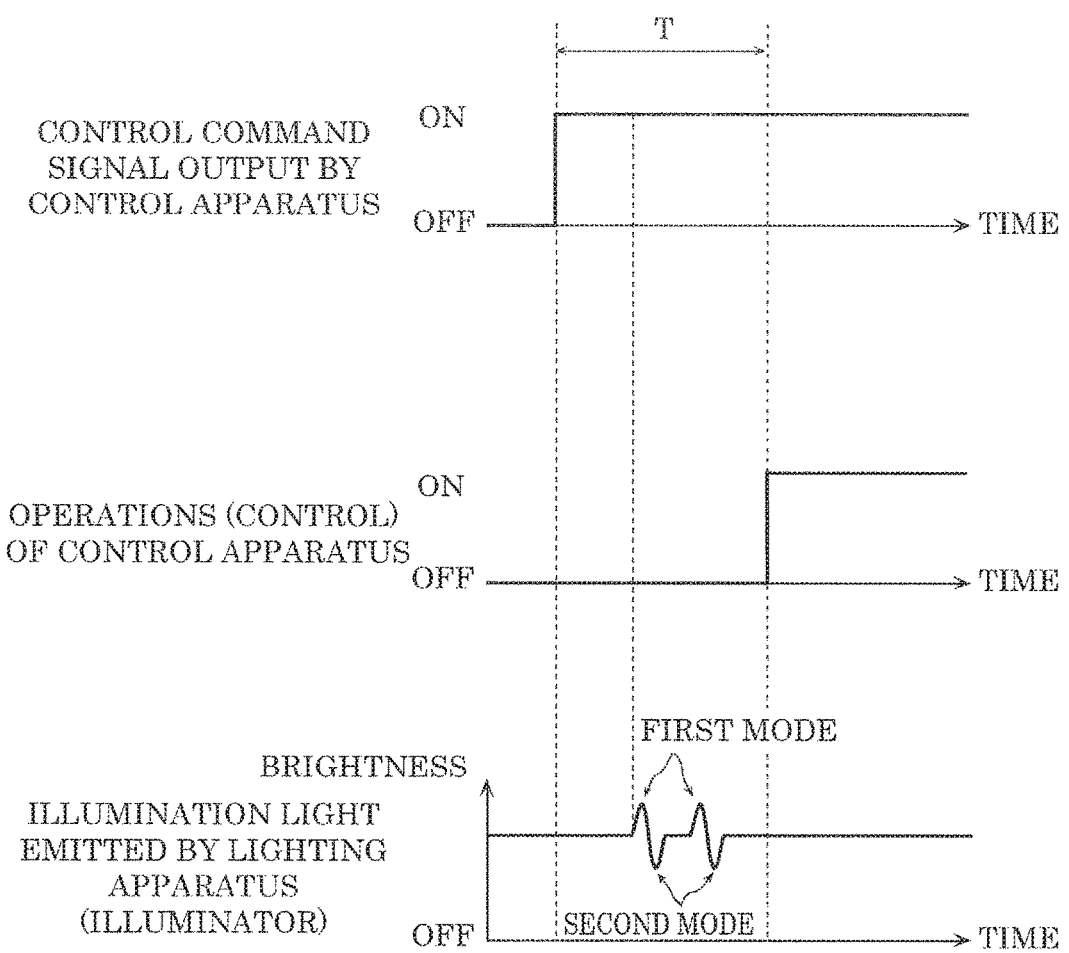
FIG. 13 is a diagram illustrating a third example of control performed by the luminaire and control performed by the control apparatus according to Embodiment 2.

In addition, as illustrated in FIG. 13, lighting controller 12 may control illuminator 11 so that illuminator 11 repeats the first mode and the second mode plural times.

In this way, it is possible to cause the user to recognize the change in brightness of the illumination light more easily than in the case where the first mode and the second mode are repeated only once.

In addition, when there are a plurality of control target apparatuses which are prevented from starting to operate for a predetermined period, it is possible to allow the user to expect that each of control target apparatuses will start to operate according to the number of repetitions of the first mode and the second mode. For example, it is possible to associate a start of an operation of control apparatus 20A with the case where the number of repetitions of the first mode and the second mode is one, and to associate a start of an operation of a control target apparatus other than control apparatus 20A with the case where the number of repetitions of the first mode and the second mode is two.

Although the same control command signal as in Embodiment 1 is used as the control command signal received by receiver 13 in this embodiment, it is to be noted that control command signals are not limited thereto. More specifically, control command signals are not limited to the ones including one or more parameters including, as an element, at least one of a brightness of illumination light emitted by illuminator 11, a color temperature of the illumination light emitted by illuminator 11, and control time for controlling the illumination light emitted by illuminator 11. In other words, in this embodiment, the light alert control may be performed using a control command signal other than the control command signal in Embodiment 1.

Variation 1 of Embodiment 2

Figure 14:
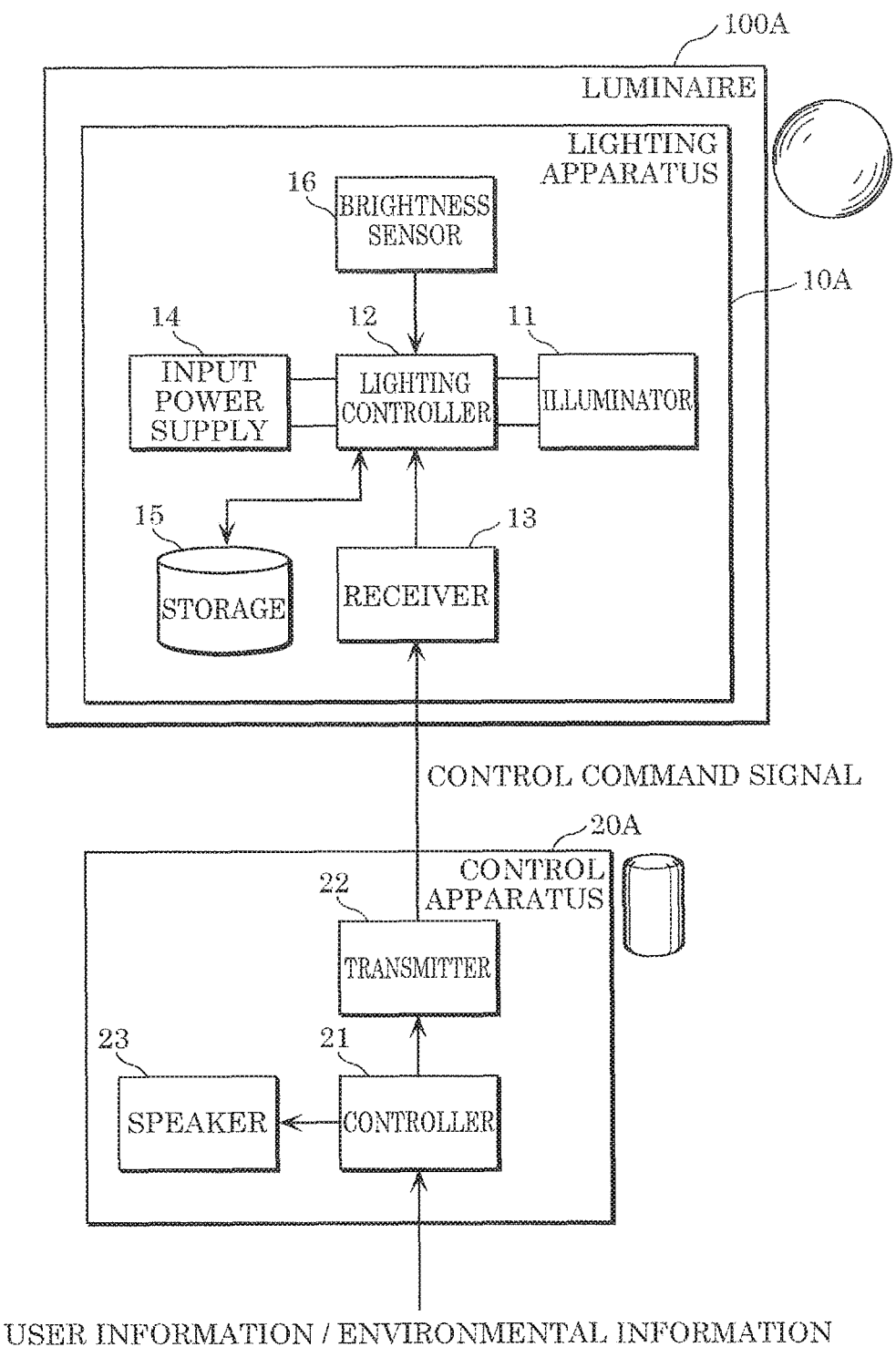
FIG. 14 is a block diagram illustrating a configuration of the lighting system according to Variation 1 of Embodiment 2.

FIG. 14 is a block diagram illustrating a configuration of the lighting system according to Variation 1 of Embodiment 2.

As illustrated in FIG. 14, luminaire 100A (lighting apparatus 10A) of the lighting system according to this variation further includes brightness sensor 16 in addition to the elements illustrated in FIG. 10. Brightness sensor 16 is, for example, an illuminance sensor.

In this way, in this embodiment, control apparatus 20A is prevented from starting to operate during the period (predetermined period T) from when control apparatus 20A transmits a control command signal to when the brightness of illumination light emitted by illuminator 11 changes, and thus the brightness of illumination light emitted by illuminator 11 changes before control apparatus 20A starts to operate.

In this way, the user can expect that control apparatus 20A will start to operate soon, and thus can be ready for the start of the operation of control apparatus 20A. Accordingly, it is possible to notify the user that control apparatus 20A will start to operate soon, by providing a small stimulus.

Figure 15:
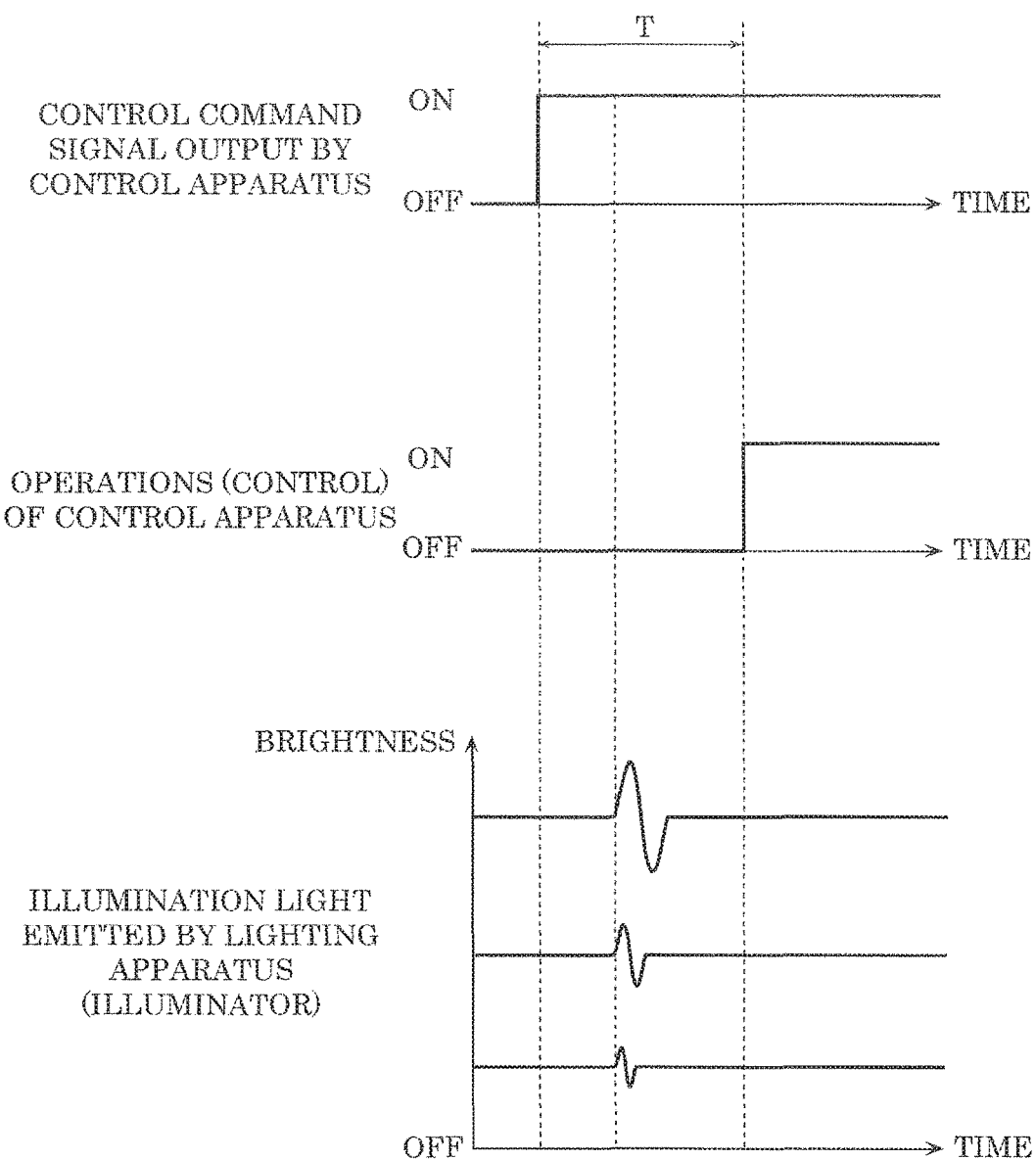
FIG. 15 is a diagram illustrating examples of control performed by the luminaire and control performed by the control apparatus according to Variation 1 of Embodiment 2.

Furthermore, in this variation, as illustrated in FIG. 15, lighting controller 12 performs a light alert control on illuminator 11 such that the brightness of illumination light changes according to the brightness (illuminance) which is sensed by brightness sensor 16.

More specifically, brightness sensor 16 senses an illuminance around lighting apparatus 10A, and, according to the sensed illuminance, lighting controller 12 changes a peak value in the first mode in which the brightness of illumination light is increased and a peak value in the second mode in which the brightness of illumination light is decreased. It is to be noted that, in FIG. 15, three control patterns for light alert control according to this variation are illustrated, and the control patterns differ from each other in the peak values in the first mode and the second mode.

In this way, it is possible to control the brightness of illumination light suitably for adaptation of user's eyes, by changing the brightness according to the illuminance sensed by brightness sensor 16. Accordingly, in this variation, it is possible to cause the user to recognize the change in the brightness of illumination light, by providing a small stimulus.

Variation 2 of Embodiment 2

Figure 16:
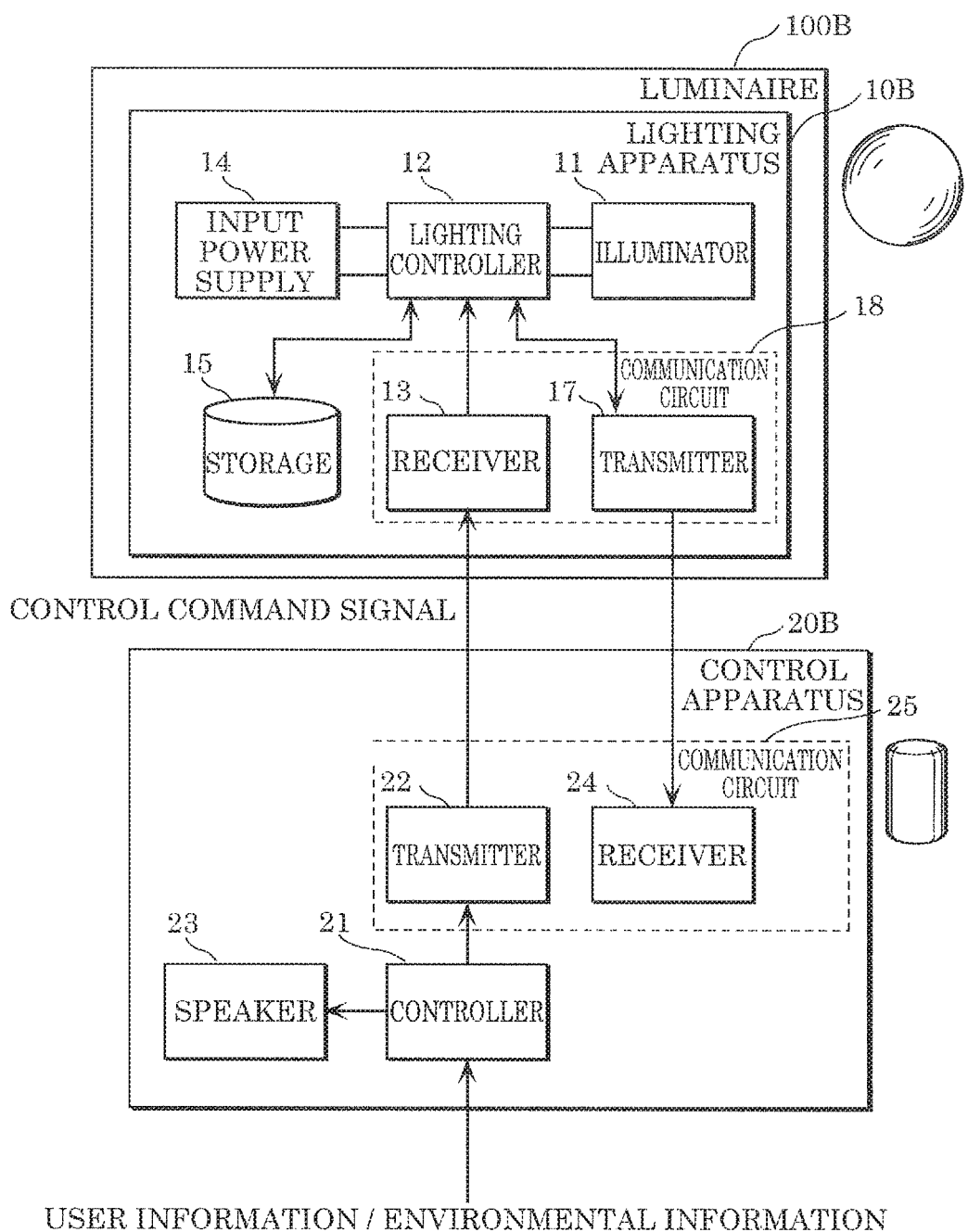
FIG. 16 is a block diagram illustrating a configuration of the lighting system according to Variation 2 of Embodiment 2.

FIG. 16 is a block diagram illustrating a configuration of the lighting system according to Variation 2 of Embodiment 2.

As illustrated in FIG. 16, luminaire 100B (lighting apparatus 10B) of the lighting system according to this variation further includes transmitter 17 in addition to the elements illustrated in FIG. 10. More specifically, lighting apparatus 10B includes communication circuit 18 including receiver 13 and transmitter 17.

In addition, in this variation, control apparatus 20B further includes receiver 24 in addition to the elements illustrated in FIG. 10. More specifically, control apparatus 20B includes communication circuit 25 including transmitter 22 and receiver 24.

In this variation, as in Embodiment 2, when receiver 13 of lighting apparatus 10B receives a control command signal from control apparatus 20B, the brightness of illumination light emitted by illuminator 11 is changed before control apparatus 20B starts to operate.

At this time, in this variation, communication circuit 18 of lighting apparatus 10B and communication circuit 25 of control apparatus 20B communicate with each other, and lighting apparatus 10B outputs, to control apparatus 20B, apparatus control signals for controlling stop and start of an operation of control apparatus 20B.

Figure 17:
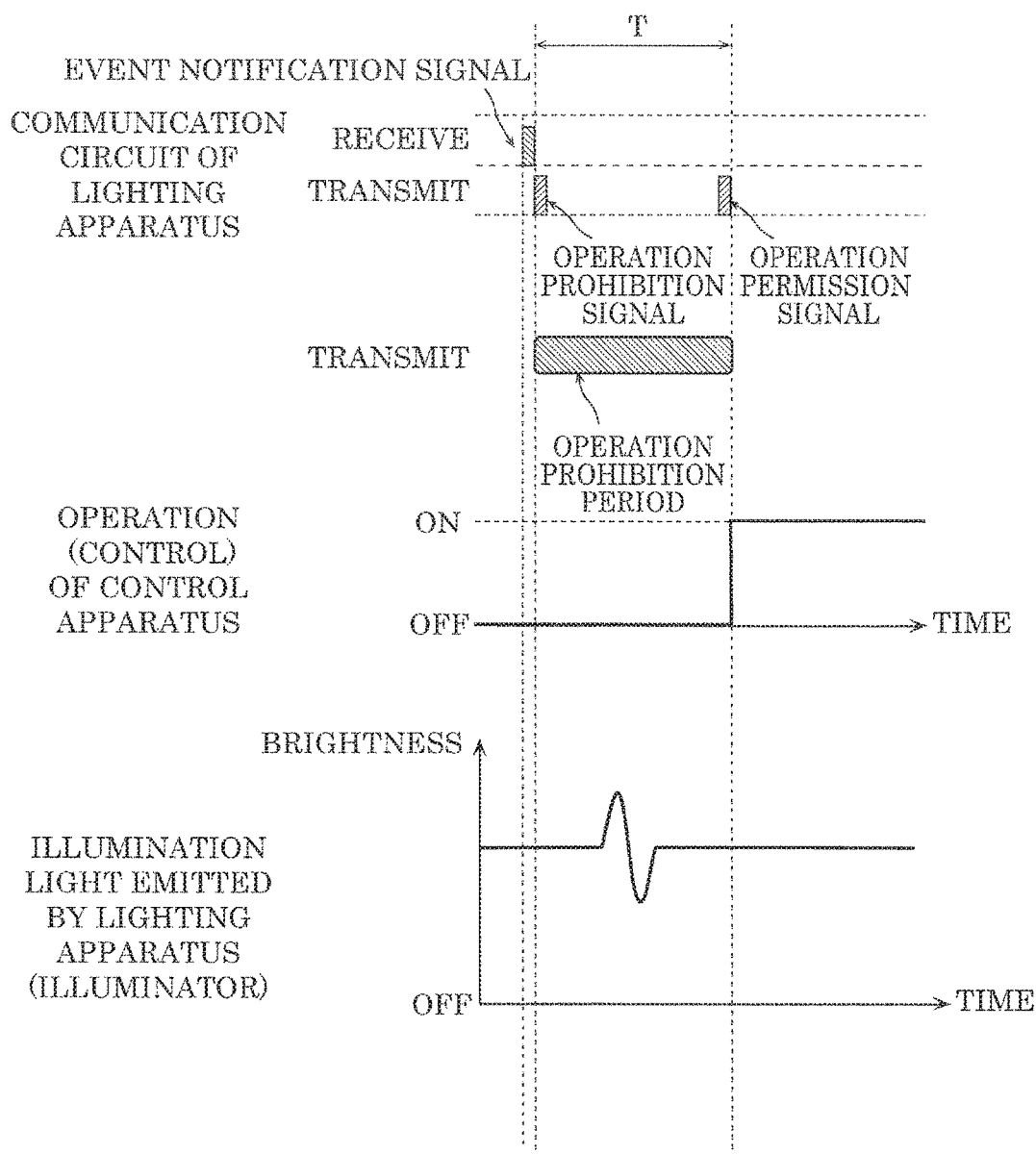
FIG. 17 is a diagram illustrating examples of control performed by the luminaire and control performed by the control apparatus according to Variation 2 of Embodiment 2.

More specifically, as illustrated in FIG. 17, when receiver 13 of lighting apparatus 10B receives a control command signal as an event notification signal from control apparatus 20B, lighting apparatus 10B (transmitter 17) transmits an operation prohibition signal for stopping the operation of control apparatus 20B to control apparatus 20B (receiver 24).

Accordingly, lighting apparatus (transmitter 17) transmits, to control apparatus 20B (receiver 24), an operation permission signal for permitting control apparatus 20B to start to operate, so that control apparatus 20B starts to operate after an elapse of predetermined operation prohibition period T. Although the operation permission signal is transmitted immediately before the elapse of operation prohibition period T in this variation, it is to be noted that the timing is not limited thereto.

In this variation, lighting apparatus 10B determines operation prohibition period T although control apparatus 20A determines operation prohibition period T in Embodiment 2 as described above. More specifically, lighting apparatus 10B transmits two signals of the operation prohibition signal and the operation permission signal to control apparatus 20B via communication circuit 18.

In this variation, in the period (operation prohibition period T) from when control apparatus 20B transmits the control command signal to when the brightness of illumination light emitted by illuminator 11 changes, control apparatus 20B is prevented from starting to operate, and the brightness of illumination light emitted by illuminator 11 changes before control apparatus 20B starts to operate.

In this way, the user can expect that control apparatus 20B will start to operate soon, and thus can be ready for the start of the operation of control apparatus 20B. Accordingly, it is possible to notify the user that control apparatus 20B will start to operate soon, by providing a small stimulus.

Although the two signals of the operation prohibition signal and the operation permission signal to control apparatus 20B are transmitted from lighting apparatus 10B (transmitter 17) to control apparatus 20B (receiver 24), this is a non-limiting example. For example, lighting apparatus 10B (transmitter 17) may transmit, to control apparatus 20B, an apparatus control signal for causing control apparatus 20B to stop an operation for a predetermined period.

Variation 3 of Embodiment 2

Figure 18:
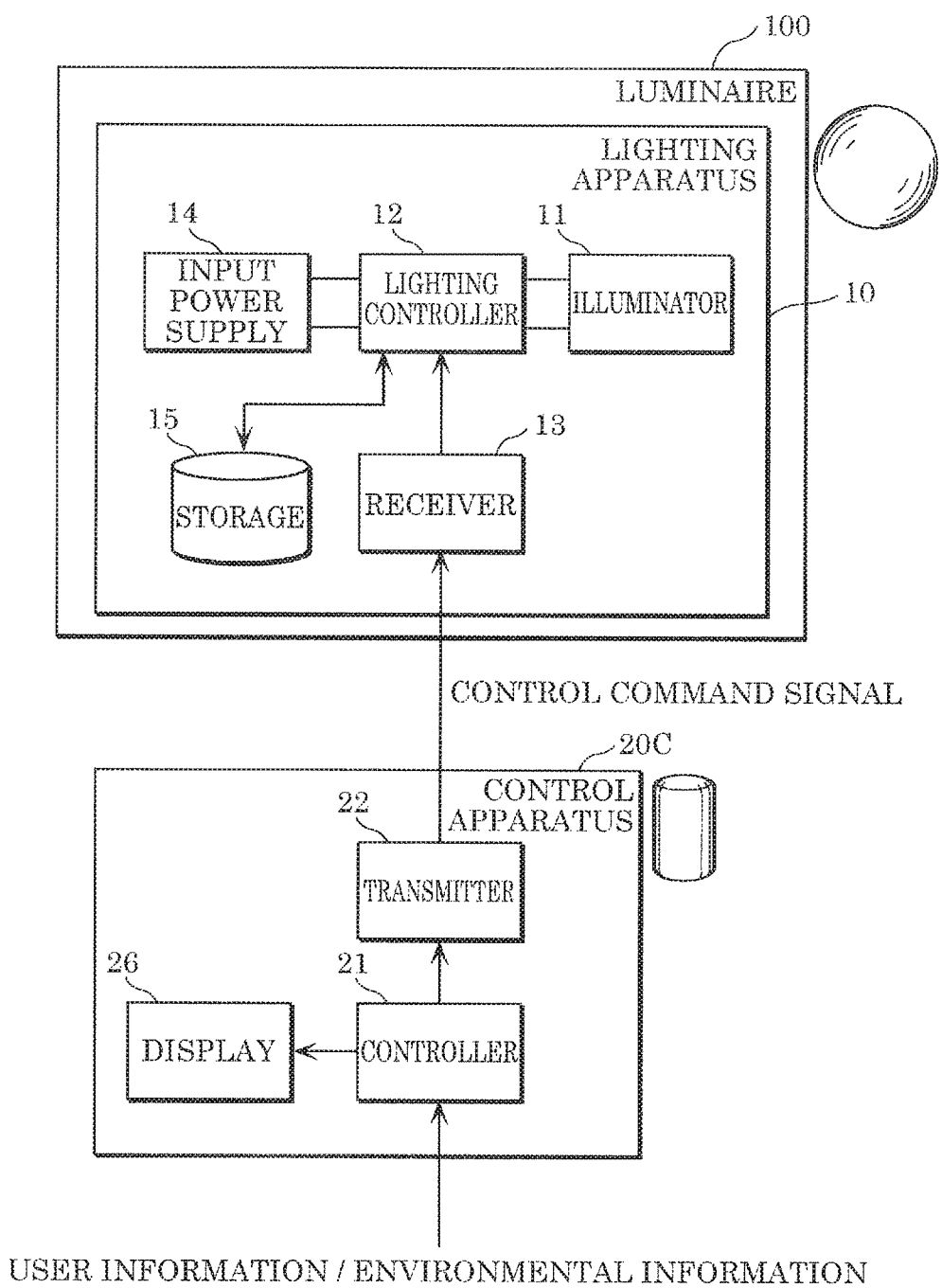
FIG. 18 is a block diagram illustrating a configuration of the lighting system according to Variation 3 of Embodiment 2.

FIG. 18 is a block diagram illustrating a configuration of the lighting system according to Variation 3 of Embodiment 2.

In Embodiment 2 illustrated in FIG. 10, control apparatus 20A includes speaker 23 as a control target, and notification using music is started after the brightness of illumination light is changed. This is a non-limiting example.

For example, as illustrated in FIG. 18, control apparatus 20C may include display 26 as a control target. Display 26 is, for example, a video display device (video display apparatus) such as a projector and a display.

In this case, when receiver 13 of lighting apparatus 10 receives a control command signal from control apparatus 20C, the brightness of illumination light emitted by illuminator 11 changes before display 26 starts to display video.

In this variation, control apparatus 20C is prevented from starting to operate during the period (predetermined period T) from when control apparatus 20C transmits a control command signal to when the brightness of illumination light that is being emitted by illuminator 11 changes, and thus the brightness of illumination light emitted by illuminator 11 changes before control apparatus 20C starts to operate.

In this way, the user can expect that control apparatus 20C will start to operate soon, and thus can be ready for the start of the operation of control apparatus 20C. For example, the user can expect that video will be displayed soon. Accordingly, it is possible to reduce the psychological burden of the user caused by an abrupt operation of control apparatus 20C, and to notify the user that control apparatus 20C will start to operate soon, by providing a small stimulus.

Variation 4 of Embodiment 2

Figure 19:
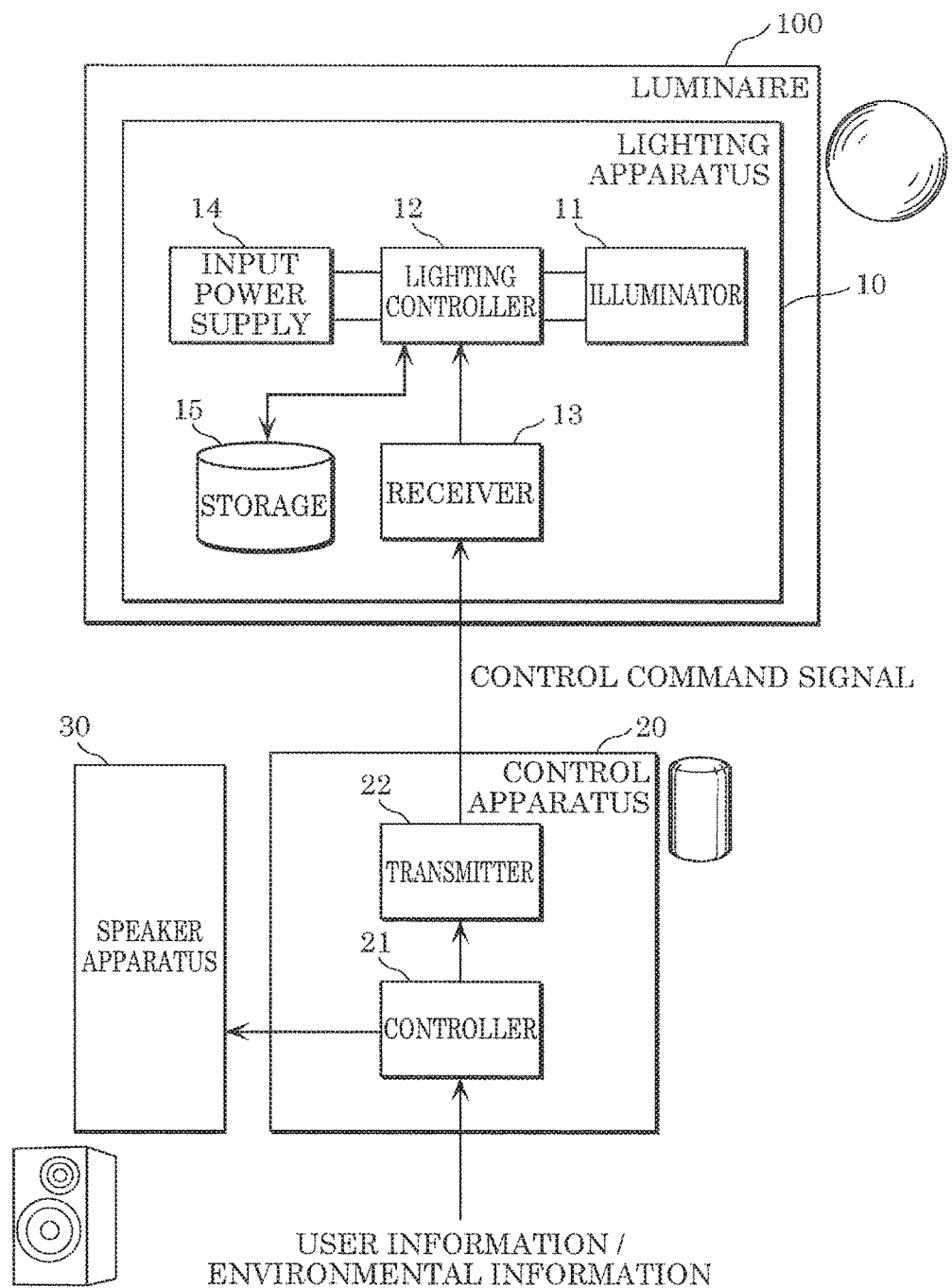
FIG. 19 is a block diagram illustrating a configuration of the lighting system according to Variation 4 of Embodiment 2.

FIG. 19 is a block diagram illustrating a configuration of the lighting system according to Variation 4 of Embodiment 2.

In Embodiment 2 illustrated in FIG. 10, the control target apparatus which starts to operate after the brightness of illumination light emitted by illuminator 11 is changed is control apparatus 20A which includes speaker 23. It is to be noted that this is a non-limiting example. In other words, the control target apparatus which starts to operate after the brightness of illumination light emitted by illuminator 11 is changed may be a body separate from control apparatus 20A.

More specifically, as illustrated in FIG. 19, it is also good to use speaker apparatus 30 having a speaker function as a control target apparatus which starts to operate after the brightness of illumination light emitted by illuminator 11 is changed. Speaker apparatus 30 is, for example, an audio apparatus having a function for reproducing music, and disposed separately from control apparatus 20.

In this variation, when transmitting a control command signal to lighting apparatus 10, control apparatus 20 transmits, also to speaker 30, a signal for preventing speaker apparatus 30 from starting to operate during predetermined period T from when control apparatus 20 transmitted a control command signal.

In this way, it is possible to change the brightness of illumination light emitted by illuminator 11 before speaker apparatus 30 starts to operate. Accordingly, the user can expect that speaker apparatus 30 will start to operate soon.

Although speaker apparatus 30 has a music reproduction function in this variation, it is to be noted that this is a non-limiting example. For example, speaker apparatus 30 may have only a speaker function. In this case, music to be reproduced is obtained from an audio apparatus having a music reproduction function.

Other Variations

Although the present disclosure has been described above based on the embodiments, the present disclosure is not limited to the above embodiments.

Figure 20:
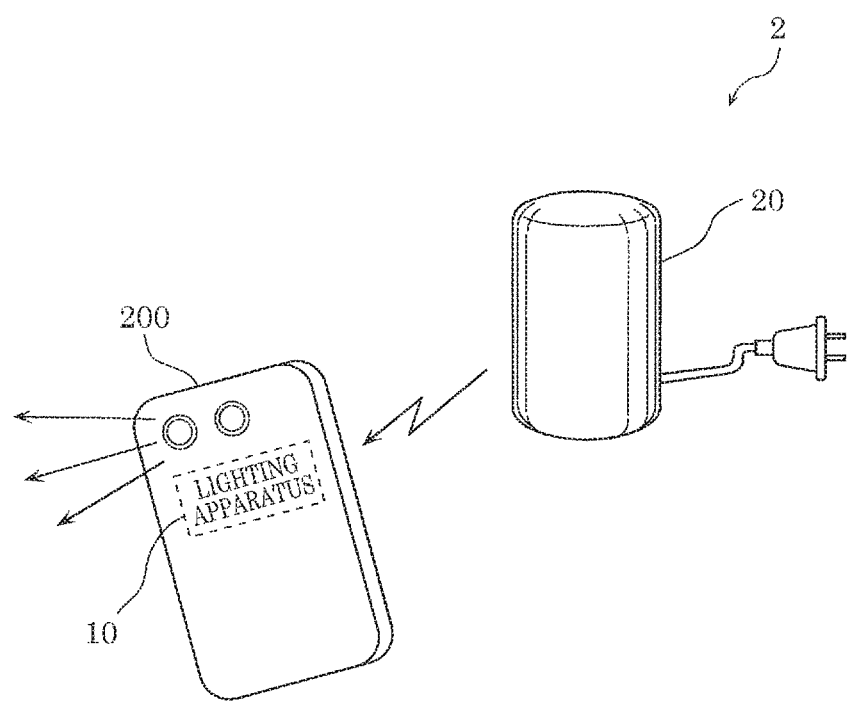
FIG. 20 is a diagram illustrating a configuration of the lighting system according to a variation.

For example, although lighting apparatus 10 is included in each of the luminaires according to the embodiment, lighting apparatus 10 may be included in mobile terminal 200 such as a smartphone as in lighting system 2 illustrated in FIG. 20. In addition, although not illustrated, lighting apparatus 10 may be included in an electronic apparatus other than mobile terminals.

In addition, although illumination light control patterns according to the light alert mode are illustrated in FIGS. 11 to 13 in Embodiment 2, illumination light control patterns according to the light alert mode are not limited thereto. For example, illumination light control patterns according to the light alert mode may include an ON/OFF (fading) of illumination light. For example, it is possible to use a light alert signal for reproducing music or displaying video after a user enters a room and illumination light fades on or becomes darker instead of reproducing the music or displaying the video as soon as the user enters the room.

In addition, although the control apparatus in Embodiment 2 includes the speaker (sound output function) or the display (display function) as the control target, this is a non-limiting example. For example, the control apparatus may have other functions such as a lighting function, an air conditioning function, etc. as a control target.

In addition, in any of the embodiments, the lighting apparatus, the speaker, and the video display device may be integrated into a unit. In this case, the integrated unit may be the control apparatus including controller 21.

In addition to these variations, the present disclosure covers embodiments obtainable by adding various kinds of modifications that a person skilled in the art would arrive at to any of the embodiments and embodiments obtainable by arbitrarily combining the constituent elements and functions in the embodiments without deviating from the scope of the present disclosure.

In addition, in the above descriptions, lighting controller 12, controller 21, etc. may be configured with circuits. These circuits may be configured as a single circuit as a whole, or as separate circuits. Each of the circuits may be a general circuit or an exclusive circuit.

In addition, the processes described as operations of lighting controller 12, controller 21, etc. may be executed by a computer. For example, the computer executes each of the processes by executing a program using hardware resources such as a processor (CPU), a memory, an input and output circuits, etc. More specifically, the processor executes each of the processes by, for example, obtaining data as a processing target from the memory, the input and output circuit, or the like, calculates the data, outputting the calculation result to the memory, the input and output circuit, or the like.

In addition, the program for executing each of the processes may be stored in a non-transitory recording medium such as a computer readable CD-ROM or the like. In this case, the computer executes each of the processes by reading out the program from the non-transitory recording medium, and executing the program. For example, it is also possible to implement the present disclosure as a program for causing the computer to execute a method performed in the lighting system, and to implement the present disclosure as a computer readable recording medium having the program recorded thereon.

It should be noted that the present disclosure can be implemented as a program for causing a computer to function as the above lighting system, and/or as a computer readable recording medium having the program stored therein.

What is claimed is:

1. A lighting apparatus, comprising:
an illuminator including a light source which emits illumination light;
a lighting controller which controls the illuminator; and
a receiver which receives, from another apparatus, a control command signal generated based on at least one of user information and environmental information in order to control the illumination light,
wherein the control command signal includes a plurality of parameters including, as elements, at least two of a brightness of the illumination light, a color temperature of the illumination light, and control time for controlling the illumination light.

2. The lighting apparatus according to claim 1,
wherein the receiver receives the control command signal which has been generated by the other apparatus based on the at least one of the user information and the environmental information which have been obtained by a sensor as sensor information.

3. The lighting apparatus according to claim 2,
wherein the other apparatus receives the sensor information transmitted from a pre-stage apparatus including the sensor.

4. The lighting apparatus according to claim 1,
wherein the receiver receives the control command signal generated by the other apparatus based on the user information and the environmental information accumulated in a cloud server.

5. The lighting apparatus according to claim 1,
wherein the user information indicates an amount of activity of a user.

6. The lighting apparatus according to claim 1,
wherein the plurality of parameters comprises a first parameter indicating the brightness of the illumination light, a second parameter indicating the color temperature of the illumination light, and a third parameter indicating the control time for controlling the illumination light.

7. The lighting apparatus according to claim 6,
wherein the first parameter, the second parameter, and the third parameter are collectively included in the control command signal and transmitted in a single transmission.

8. The lighting apparatus according to claim 1,
wherein one of the plurality of parameters includes all elements which are the brightness of the illumination light, the color temperature of the illumination light, and the control time for controlling the illumination light.

9. The lighting apparatus according to claim 1,
wherein when the lighting controller changes a first set value indicating a current value of one of the brightness and the color temperature of the illumination light that is being emitted by the illuminator to a second set value indicating a target value of one of the brightness and the color temperature of the illumination light indicated in the control command signal, the lighting controller changes the current value of the one of the brightness and the color temperature of the illumination light while changing the first set value to the second set value.

10. The lighting apparatus according to claim 9,
wherein the number of control patterns for changing the illumination light having the first set value to the illumination light having the second set value is two or more, and
the lighting controller selects a control pattern from among the two or more control patterns according to the control command signal, and changes the illumination light having the first set value to the illumination light having the second set value according to the selected control pattern.

11. The lighting apparatus according to claim 10,
wherein at least one of the two or more control patterns include a pattern for performing fluctuation control for repeating a mode for increasing the brightness of the illumination light and a mode for decreasing the brightness of the illumination light.

12. The lighting apparatus according to claim 10,
wherein at least one of the two or more control patterns include a pattern for performing light alarm control for gradually increasing the brightness of the illumination light.

13. The lighting apparatus according to claim 12,
wherein, in the light alarm control, boost control for drastically changing the brightness of the illumination light is performed, and
the boost control is performed by performing dimming and toning control for changing at least one of the brightness of the illumination light and the color temperature of the illumination light.

14. The lighting apparatus according to claim 10,
wherein at least one of the two or more control patterns is a pattern for performing light alert control for notifying a user that a predetermined control target apparatus will start to operate by changing the brightness of the illumination light.

15. The lighting apparatus according to claim 1,
wherein the lighting apparatus has:
a turn-off mode for turning off the light source;
a dimming and toning mode for changing at least one of the brightness of the illumination light and the color temperature of the illumination light;
a light alarm mode for gradually increasing the brightness of the illumination light;
a light alert mode for notifying a user that a predetermined control target apparatus will start to operate by changing the brightness of the illumination light; and
a fluctuation mode for repeating a state for increasing the brightness of the illumination light and a state for decreasing the brightness of the illumination light, and
each of the light alarm mode, the light alert mode, and the fluctuation mode transits to one of the dimming and toning mode and the turn-off mode.

16. The lighting apparatus according to claim 1,
wherein when the receiver has received the control command signal from the other apparatus, and
the lighting controller changes the brightness of the illumination light by performing light alert control on the illuminator before a control target apparatus starts to operate, the control target apparatus being different from the lighting apparatus.

17. The lighting apparatus according to claim 16,
wherein the control target apparatus is the other apparatus.

18. The lighting apparatus according to claim 16,
wherein the lighting controller performs light alert control on the illuminator so that transitions to a first mode and a second mode are made in sequence, and a state of the illuminator returns to a state before the control command is received, the first mode being for increasing the brightness of the illumination light and the second mode being for decreasing the brightness of the illumination light to be lower than the brightness in the first mode.

19. The lighting apparatus according to claim 18,
wherein the lighting controller controls the illuminator so that the illuminator repeats the first mode and the second mode plural times.

20. The lighting apparatus according to claim 18,
wherein the illuminator includes the light source comprising a plurality of light sources having mutually different color temperatures, and
the lighting controller controls the illuminator such that a color temperature of the illumination light in the first mode is higher than a color temperature of the illumination light in the second mode.

21. The lighting apparatus according to claim 20,
wherein the lighting controller controls the illuminator such that the color temperature of the illumination light changes gradually.

22. The lighting apparatus according to claim 6, further comprising:
a brightness sensor,
wherein the lighting controller performs the light alert control on the illuminator such that the brightness of the illumination light changes according to the brightness which is sensed by the brightness sensor.

23. The lighting apparatus according to claim 16, further comprising:
a transmitter,
wherein the transmitter outputs, to the other apparatus, apparatus control signals for controlling stop and start of an operation of the other apparatus.

24. The lighting apparatus according to claim 16, further comprising:

a transmitter,
wherein the transmitter transmits, to the other apparatus, an apparatus control signal for causing the other apparatus to stop an operation for a predetermined period.

25. A luminaire comprising the lighting apparatus according to claim 1.

26. An electronic apparatus comprising the lighting apparatus according to claim 1.

* * * * *